(12) United States Patent
Johnson et al.

(10) Patent No.: US 12,293,820 B2
(45) Date of Patent: May 6, 2025

(54) METHODS AND APPARATUS FOR DETERMINING RADIOABLATION TREATMENT

(71) Applicants: VARIAN MEDICAL SYSTEMS, INC., Palo Alto, CA (US); VARIAN MEDICAL SYSTEMS INTERNATIONAL AG, Cham (CH)

(72) Inventors: Leigh Scott Johnson, Chicago, IL (US); Patrik Niklaus Kunz, Baden (CH); Andrea Morgan, Seattle, WA (US); Francesca Attanasi, Baar (CH); Stefan Georg Scheib, Waedenswil (CH); Jonas Honegger, Zurich (CH)

(73) Assignees: VARIAN MEDICAL SYSTEMS, INC., Palo Alto, CA (US); SIEMENS HEALTHINEERS INTERNATIONAL AG, Cham (CH)

( * ) Notice: Subject to any disclaimer, the term of this patent is extended or adjusted under 35 U.S.C. 154(b) by 495 days.

(21) Appl. No.: 17/640,618

(22) PCT Filed: Jul. 3, 2020

(86) PCT No.: PCT/US2020/040812
§ 371 (c)(1),
(2) Date: Mar. 4, 2022

(87) PCT Pub. No.: WO2022/005488
PCT Pub. Date: Jan. 6, 2022

(65) Prior Publication Data
US 2022/0351836 A1  Nov. 3, 2022

(51) Int. Cl.
*G16H 30/40* (2018.01)
*G06T 17/20* (2006.01)
*G06V 10/26* (2022.01)

(52) U.S. Cl.
CPC ............. *G16H 30/40* (2018.01); *G06T 17/20* (2013.01); *G06V 10/26* (2022.01); *G06T 2210/41* (2013.01)

(58) Field of Classification Search
CPC ..... G16H 30/40; G06T 17/20; G06T 2210/41; G06T 19/00; G06V 10/26
See application file for complete search history.

(56) References Cited

U.S. PATENT DOCUMENTS

| | | | |
|---|---|---|---|
| 11,922,634 B2* | 3/2024 | Peters | G06T 7/149 |
| 2005/0143965 A1* | 6/2005 | Failla | G01T 1/02 |
| | | | 703/2 |

(Continued)

FOREIGN PATENT DOCUMENTS

| | | |
|---|---|---|
| CN | 104318554 A | 1/2015 |
| CN | 107072595 A | 8/2017 |

(Continued)

OTHER PUBLICATIONS

Sung et al. Dose Gradient Curve: A New Tool for Evaluating Dose Gradient (Year: 2018).*

(Continued)

*Primary Examiner* — John B Strege
(74) *Attorney, Agent, or Firm* — Duane Morris LLP

(57) ABSTRACT

Systems and methods for cardiac radioablation treatment planning are disclosed. In some examples, a computing device receives an image volume and a dose matrix data. The computing device generates a first mesh of organ substructures for the organ based on substructure contours for the organ. Further, the computing device generates a second mesh of an isodose volume based on the dose matrix data. The computing device displays the first mesh of the organ substructures and the second mesh of the isodose volume within a same scene. In some examples, the computing device samples a plurality of dosage values, deter- (Continued)

mines representative dosage values for each of a plurality of points along surfaces of a dose matrix, and generates an image for display based on the representative dosage values. In some examples, a segmentation model is generated for display based on the representative dosage values.

20 Claims, 13 Drawing Sheets

(56) References Cited

U.S. PATENT DOCUMENTS

| | | | |
|---|---|---|---|
| 2008/0004543 | A1 | 1/2008 | Davies |
| 2011/0166408 | A1* | 7/2011 | Sumanaweera ......... G06T 15/08 600/1 |
| 2013/0058460 | A1* | 3/2013 | Weigand .............. A61N 5/1031 378/65 |
| 2013/0083004 | A1* | 4/2013 | Nord .................... A61N 5/1031 345/419 |
| 2013/0113802 | A1 | 5/2013 | Weersink et al. |
| 2013/0289332 | A1* | 10/2013 | Purdie .................. A61N 5/1039 600/1 |
| 2014/0022250 | A1 | 1/2014 | Mansi et al. |
| 2014/0171791 | A1 | 6/2014 | Simon et al. |
| 2014/0282008 | A1 | 9/2014 | Verard et al. |
| 2016/0332000 | A1* | 11/2016 | Hale ........................ G01T 1/29 |
| 2016/0339268 | A1* | 11/2016 | Bzdusek ............. A61N 5/1047 |
| 2018/0063386 | A1* | 3/2018 | Sharma .................. H04N 23/60 |
| 2019/0012066 | A1* | 1/2019 | Ahonen .................. G06T 19/20 |
| 2022/0288420 | A1* | 9/2022 | Brown ................. A61N 5/1049 |
| 2023/0181929 | A1* | 6/2023 | Sung .................... A61N 5/1031 600/1 |

FOREIGN PATENT DOCUMENTS

| | | |
|---|---|---|
| WO | 2010064154 A1 | 6/2010 |
| WO | 2011009121 A1 | 1/2011 |
| WO | 2017078757 A1 | 5/2017 |
| WO | 2019055491 A1 | 3/2019 |
| WO | 2019118640 A1 | 6/2019 |

OTHER PUBLICATIONS

Lobos et al. Techniques for the generation of 3D finite element meshes of human organs (Year: 2009).*

Third Party Observations for European Patent Application No. 20746499.1 dated Feb. 29, 2024, 3 pages.

Blanck, et al., "Radiosurgery for ventricular tachycardia: preclinical and clinical evidence and study design for a German multi-center mult••platform feasibility trial (RAVENTA)," Apr. 18, 2020. Clinical Research in Cardiology, 109 (11): 1319-1332.

Brett, et al., "Novel Workflow for Conversion of Catheter-Based Electroanatomic Mapping to DICOM Imaging for Noninvasive Radioablation of Ventricular Tachycardia," May 13, 2020. Pract Radiat Oncol., 11(1):84-88.

Wei, et al., "Non-invasive Stereotactic Radioablation: A New Option for the Treatment of Ventricular Arrhythmias," Feb. 12, 2020. Arrhythm Electrophysiol Rev., 8(4):285-293.

Anonymous, "Remote Desktop Software-Wikipedia" Jun. 26, 2020 (Jun. 26, 2020), XP055727436, Retrieved from the Internet: URL:https://en.wikipedia.org/w/index.php?title= Remote_desktop_software &oldid=9645967 74 [retrieved on Sep. 3, 2020].

Zellmer, et al., "The Shortage of radiation oncology physicists is addressable through remote treatment planning combined with periodic visits by consultant physicists", Medical Physics, AIP, Melville, NY, US, vol. 35, No. 4, Mar. 2008, pp. 1167-1169.

International Search Report and Written Opinion for PCT International Application No. PCT/US2020/040808 dated Mar. 18, 2021, 14 pages.

International Search Report and Written Opinion for PCT International Application No. PCT/US2020/040812 dated Apr. 23, 2021, 14 pages.

Ferrante, et al., "Slice-to-volume medical image registration: A survey", Medical Image Analysis, Apr. 2017, 39: 101-123.

Schwein, et al., "Feasibility of three-dimensional magnetic resonance angiography-fluoroscopy image fusion technique in guiding complex endovascular aortic procedures in patients with renal insufficiency", Journal of Vascular Surgery, Dec. 2016, 65(5): 1440-1452.

Anonymous, "Medical Imaging Interaction Toolkit: The Rigid Registration View", Dec. 2019, Retrieved from the Internet: URL:https://web.archive.org/web/2019121009 4930/https://docs.mitk.org/2016.11/org_mitk_views_rigidregistration.html [retrieved on Sep. 2, 2021], 7 pages.

Anonymous, "Optimized automatic registration 3D-MIPAV", Oct. 2013, Retrieved from the Internet: URL:https://web.archive.org/web/2013102904 1146/https://mipav.cit.nih.gov/pubwiki/index.php/Optimized_automatic_registration_3D [retrieved on Sep. 2, 2021], 12 pages.

Sawaneh, et al., "A Computerized Patient's Database Management System" International Journal of Computer Science and Information Technology Research, Apr.-Jun. 2018, 6(2): 6-10.

Asabe, "Hospital Patient Database Management System" Compusoft, Mar. 2013, 2(3): 65-72.

International Search Report and Written Opinion for PCT International Application No. PCT/US2020/066213 dated Dec. 22, 2021, 21 pages.

* cited by examiner

METHODS AND APPARATUS FOR DETERMINING RADIOABLATION TREATMENT

CROSS-REFERENCE TO RELATED APPLICATIONS

This application is a National Stage Application, filed under 35 U.S.C. 371, of International Patent Application No. PCT/US2020/040812, filed on Jul. 3, 2020 the disclosure of which is incorporated herein by reference in its entirety.

FIELD

Aspects of the present disclosure relate in general to medical diagnostic and treatment systems and, more particularly, to providing radioablation diagnostic, treatment planning, and delivery systems for diagnosis and treatment of conditions, such as cardiac arrhythmias.

BACKGROUND

Various technologies can be employed to capture or image a patient's metabolic, electrical and anatomical information. For example, positron emission tomography (PET) is a metabolic imaging technology that produces tomographic images representing the distribution of positron emitting isotopes within a body. Computed Tomography (CT) and Magnetic Resonance Imaging (MRI) are anatomical imaging technologies that create images using x-rays and magnetic fields respectively. Images from these exemplary technologies can be combined with one another to generate composite anatomical and functional images. For example, software systems, such as Velocity™ software from Varian Medical Systems, Inc. combine different types of images using an image fusion process to deform and/or register images to produce a combined image.

In cardiac radioablation, medical professionals work together to diagnose cardiac arrhythmias, identify regions for ablation, prescribe radiation treatment, and create radioablation treatment plans. Typically, each of the various medical professionals have complementary medical training and thus specialize in varying aspects of the treatment development. For example, an electrophysiologist may identify one or more regions or targets of a patient's heart for treatment of cardiac arrhythmias based on a patient's anatomy and electrophysiology. The electrophysiologist may use, for example, combined PET and cardiac CT images as inputs to manually define a target region for ablation. Once a target region is defined by the electrophysiologist, a radiation oncologist may prescribe radiation treatment including, for example, the number of fractions of radiation to be delivered, radiation dose to be delivered to a target region and maximum dose to adjacent organs at risk. Once a radiation dose is prescribed, typically a dosimetrist may create a radioablation treatment plan based on the prescribed radiation therapy. The radiation oncologist then typically reviews and approves the treatment plan to be delivered. Prior to delivery of the radioablation treatment plan, the electrophysiologist may want to understand the location, size, and shape of a dose region of the defined target volume to confirm the target location for the patient as defined by the radioablation treatment plan is correct.

Each medical professional uses systems designed to accomplish that medical professional's tasks within the cardiac radioablation workflow. For example, an electrophysiologist may work within one system that allows for the viewing of 3-dimensional (3D) rendered surfaces and images from systems such as cardiac CT images, cardiac MR images, and PET/CT images. An electrophysiologist may be comfortable with viewing 3D images, such as 3D surface renderings. On the other hand, a radiation therapy professional may instead work within specialized systems such as treatment planning systems that record the radiation treatment prescription or treatment objectives and optimize treatment plans to closely meet those objectives. Aspects of treatment planning systems may include importing and display of previously acquired two-dimensional (2D) planning CT or MR images, inputting the radiation therapy prescription including treatment objections and constraints, contouring or segmenting the target region to be irradiated on 3D renderings using stacked 2D CT slices, optimizing the treatment plan in relation to the radiotherapy prescription, and exporting the treatment plan to radiation delivery systems. There are opportunities to improve cardiac radioablation treatment planning systems used by medical professionals for cardiac radioablation diagnosis and radiation treatment planning.

SUMMARY

Systems and methods for cardiac radioablation diagnosis treatment and planning are disclosed. In some examples, a computer-implemented method includes receiving substructure data identifying substructure contours for an organ, and dose matrix data for the organ. The method also includes generating a first mesh of organ substructures for the organ based on the substructure data. The method also includes generating a second mesh of an isodose volume based on the dose matrix data. Further, the method includes displaying the first mesh of the organ substructures and the second mesh of the isodose volume within a same scene or workspace.

In some examples, a non-transitory computer readable medium storing instructions that, when executed by at least one processor, cause the at least one processor to perform operations including receiving substructure data identifying substructure contours for an organ, and dose matrix data for the organ. The operations also include generating a first mesh of organ substructures for the organ based on the substructure data. Further, the operations include generating a second mesh of an isodose volume based on the dose matrix data. The operations also include displaying the first mesh of the organ substructures and the second mesh of the isodose volume within a same scene or workspace.

In some examples, a system includes a computing device that is configured to receive substructure data identifying substructure contours for an organ, and dose matrix data for the organ. The computing device is also configured to generate a first mesh of organ substructures for the organ based on the substructure data. Further, the computing device is configured to generate a second mesh of an isodose volume based on the dose matrix data. The computing device is also configured to display the first mesh of the organ substructures and the second mesh of the isodose volume within a same scene or workspace.

In some examples, a method includes a means for receiving substructure data identifying substructure contours for an organ, and dose matrix data identifying a dosage for the organ. The method also includes a means for generating a first mesh of organ substructures for the organ based on substructure data. The method also includes a means for generating a second mesh of an isodose volume based on the dose matrix data. Further, the method includes a means for displaying the first mesh of the organ substructures and the second mesh of the isodose volume within a same scene or workspace.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein.

DETAILED DESCRIPTION

Figure 1:
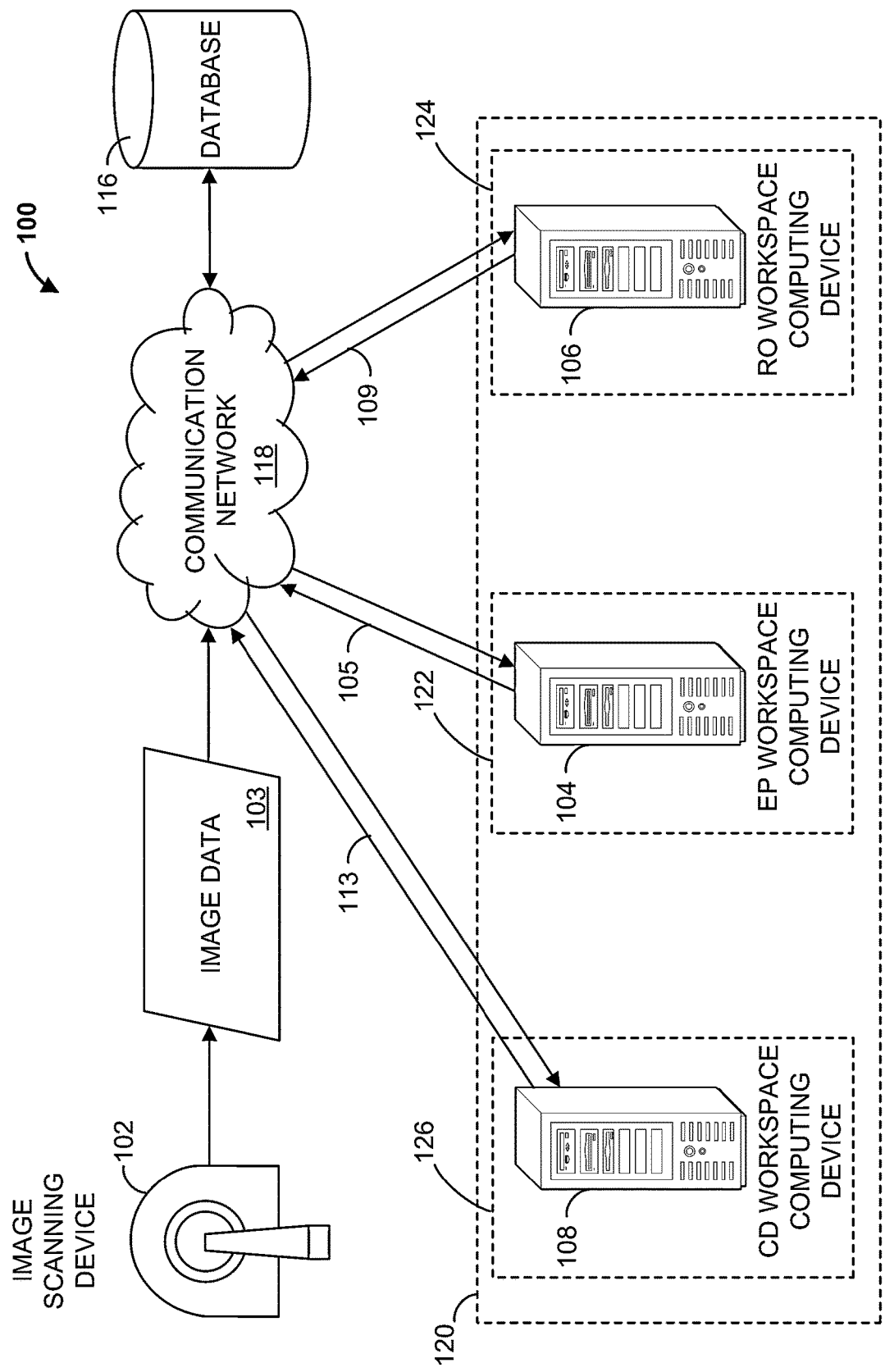
FIG. 1 illustrates a cardiac radioablation treatment planning system, in accordance with some embodiments.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

Turning to the drawings, FIG. 1 illustrates a block diagram of a radioablation diagnosis and treatment planning system 100. In some embodiments, system 100 can be a cardiac diagnosis and treatment planning system that includes an imaging device 102, an electrophysiologist (EP) workspace computing device 104, a radiation oncologist (RO) workspace computing device 106, a shared EP and RO workspace computing device 108, and a database 116 communicatively coupled over communication network 118. Imaging device 102 may be, for example, a CT scanner, an MR scanner, a PET scanner, an electrophysiologic imaging device, an ECG, or an ECG imager. In some examples, imaging device 102 may be PET/CT scanner or a PET/MR scanner.

EP workspace computing device 104, RO workspace computing device 106, and shared EP and RO workspace computing device 108 can each be any suitable computing device that includes any suitable hardware or hardware and software combination for processing data. For example, each can include one or more processors, one or more field-programmable gate arrays (FPGAs), one or more application-specific integrated circuits (ASICs), one or more state machines, digital circuitry, or any other suitable circuitry. In addition, each can transmit data to, and receive data from, communication network 118. For example, each of EP workspace computing device 104, RO workspace computing device 106, and shared EP and RO workspace computing device 108 can be a server such as a cloud-based server, a computer, a laptop, a mobile device, a workstation, or any other suitable computing device.

Figure 2:
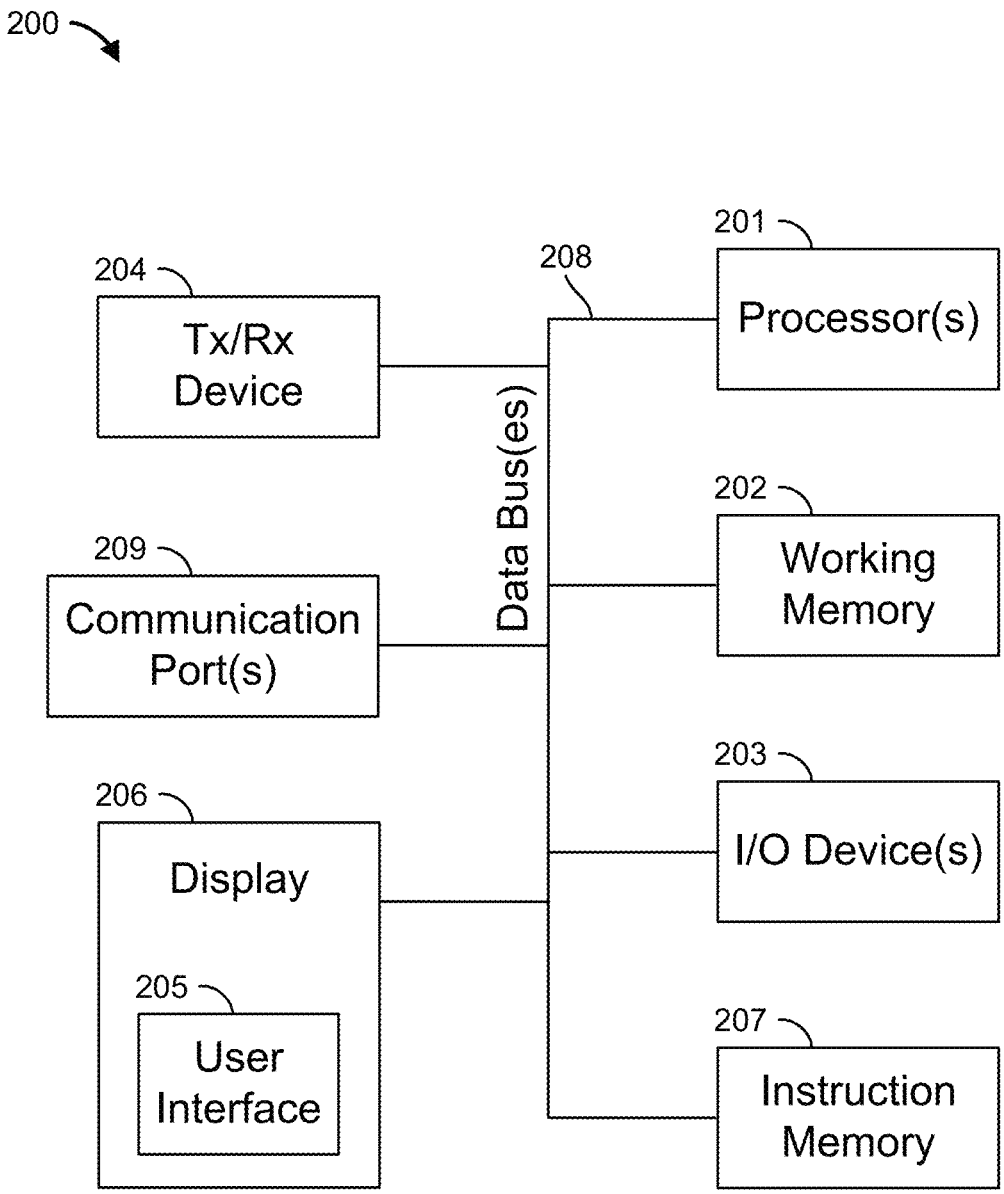
FIG. 2 illustrates a block diagram of a radioablation treatment planning computing device, in accordance with some embodiments.

For example, FIG. 2 illustrates a radioablation diagnosis and treatment planning computing device 200 that can include one or more of an EP workspace computing device 104, RO workspace computing device 106, and shared EP and RO workspace computing device 108. With reference to FIG. 2, radioablation diagnosis and treatment planning computing device 200 can include one or more processors 201, working memory 202, one or more input/output devices 203, instruction memory 207, a transceiver 204, one or more communication ports 207, and a display 206, all operatively coupled to one or more data buses 208. Data buses 208 allow for communication among the various devices. Data buses 208 can include wired, or wireless, communication channels.

Processors 201 can include one or more distinct processors, each having one or more cores. Each of the distinct processors can have the same or different structure. Processors 201 can include one or more central processing units (CPUs), one or more graphics processing units (GPUs), application specific integrated circuits (ASICs), digital signal processors (DSPs), and the like.

Instruction memory 207 can store instructions that can be accessed (e.g., read) and executed by processors 201. For example, instruction memory 207 can be a non-transitory, computer-readable storage medium such as a read-only memory (ROM), an electrically erasable programmable read-only memory (EEPROM), flash memory, a removable disk, CD-ROM, any non-volatile memory, or any other suitable memory. Processors 201 can be configured to perform a certain function or operation by executing code, stored on instruction memory 207, embodying the function or operation. For example, processors 201 can be configured to execute code stored in instruction memory 207 to perform one or more of any function, method, or operation disclosed herein.

Additionally processors 201 can store data to, and read data from, working memory 202. For example, processors 201 can store a working set of instructions to working memory 202, such as instructions loaded from instruction memory 207. Processors 201 can also use working memory 202 to store dynamic data created during the operation of radioablation diagnosis and treatment planning computing device 200. Working memory 202 can be a random access memory (RAM) such as a static random access memory (SRAM) or dynamic random access memory (DRAM), or any other suitable memory.

Input-output devices 203 can include any suitable device that allows for data input or output. For example, input-output devices 203 can include one or more of a keyboard, a touchpad, a mouse, a stylus, a touchscreen, a physical button, a speaker, a microphone, or any other suitable input or output device.

Communication port(s) 209 can include, for example, a serial port such as a universal asynchronous receiver/transmitter (UART) connection, a Universal Serial Bus (USB) connection, or any other suitable communication port or connection. In some examples, communication port(s) 209 allows for the programming of executable instructions in instruction memory 207. In some examples, communication port(s) 209 allow for the transfer (e.g., uploading or downloading) of data, such as image data.

Display 206 can be any suitable display, such as a 3D viewer or a monitor. Display 206 can display user interface 205. User interfaces 205 can enable user interaction with radioablation diagnosis and treatment planning computing device 200. For example, user interface 205 can be a user interface for an application that allows a user (e.g., a medical professional) to view or manipulate scanned images. In some examples, the user can interact with user interface 205 by engaging input-output devices 203. In some examples, display 206 can be a touchscreen, where user interface 205 is displayed on the touchscreen. In some examples, display 206 displays images of scanned image data (e.g., image slices).

Transceiver 204 allows for communication with a network, such as the communication network 118 of FIG. 1. For example, if communication network 118 of FIG. 1 is a cellular network, transceiver 204 is configured to allow communications with the cellular network. In some examples, transceiver 204 is selected based on the type of communication network 118 radioablation diagnosis and treatment planning computing device 200 will be operating in. Processor(s) 201 is operable to receive data from, or send data to, a network, such as communication network 118 of FIG. 1, via transceiver 204

Referring back to FIG. 1, database 116 can be a remote storage device (e.g., including non-volatile memory), such as a cloud-based server, a disk (e.g., a hard disk), a memory device on another application server, a networked computer, or any other suitable remote storage. In some examples, database 116 can be a local storage device, such as a hard drive, a non-volatile memory, or a USB stick, to one or more of EP workspace computing device 104, RO workspace computing device 106, and shared EP and RO workspace computing device 108.

Communication network 118 can be a WiFix network, a cellular network such as a 3GPP® network, a Bluetooth® network, a satellite network, a wireless local area network (LAN), a network utilizing radio-frequency (RF) communication protocols, a Near Field Communication (NFC) network, a wireless Metropolitan Area Network (MAN) connecting multiple wireless LANs, a wide area network (WAN), or any other suitable network. Communication network 118 can provide access to, for example, the Internet.

Imaging device 102 is operable to scan images, such as images of a patient's organs, and provide image data 103 (e.g., measurement data) identifying and characterizing the scanned images to communication network 118. Alternatively, imaging device 102 is operable to acquire electrical imaging such as cardiac ECG images. For example, imaging device 102 may scan a patient's structure (e.g., organ), and may transmit image data 103 identifying one or more slices of a 3D volume of the scanned structure over communication network 118 to one or more of EP workspace computing device 104, RO workspace computing device 106, and shared EP and RO workspace computing device 108. In some examples, imaging device 102 stores image data 103 in database 116, one or more of EP workspace computing device 104, RO workspace computing device 106, and shared EP and RO workspace computing device 108 may retrieve the image data 103 from database 116.

In some examples, EP workspace computing device 104 is operable to communicate with one or more of RO workspace computing device 106 and shared EP and RO workspace computing device 108. Similarly, in some examples RO workspace computing device 106 is operable to communication with one or more of EP workspace computing device 104 and shared EP and RO workspace computing device 108. In some examples, shared EP and RO workspace computing device 108 is operable to communicate with one or more of EP workspace computing device 104 and RO workspace computing device 106. In some examples, one or more of EP workspace computing device 104, RO workspace computing device 106, and shared EP and RO workspace computing device 108 communicate with each other via database 116 (e.g., by storing and retrieving data from database 116).

In some examples, an electrophysiologist operates EP workspace computing device 104, while a radiation oncologist operates a RO workspace computing device 106 and one or more of the electrophysiologist and radiation oncologist operates a shared EP and RO workspace computing device 108. In some examples, one or more EP workspace computing devices 104 are located in a first area 122 of a medical facility 120, while one or more RO workspace computing devices 106 are located in a second area 124 of the medical facility 120 and one or more shared EP and RO workspace computing devices 108 are located in a third area 126 of the medical facility 120. Although optionally illustrated as part of medical facility 120, in some examples, one or more of each of EP workspace computing device 104, RO workspace computing device 106, and shared EP and RO workspace computing device 108 may be located in separate medical facilities. In some examples, one or more of EP workspace computing device 104, RO workspace computing device 106, and shared EP and RO workspace computing device 108 share resources, such as processing resources, memory resources, software (e.g., applications), or any other resources, and/or communicate with each other, via the cloud. For example, each of EP workspace computing device 104, RO workspace computing device 106, and shared EP and RO workspace computing device 108 may be part of a cloud-based network that allows for the sharing of resources and communication with each device.

EP workspace computing device 104 may allow an electrophysiologist to view 3D images, such as 3D images generated from image data 103, and may also allow for the viewing of multi-modality images and fusion (e.g., cardiac CT scans, cardiac MR scans, echocardiogram, ECGI electrical maps, PET/CT scans, single photon emission computed tomography (SPECT) scans) as well as organ structure (e.g., segmentation) models, such as a 17 segment model representing a basal level, mid-cavity level, and cardiac apex of a heart's ventricle. RO workspace computing device 106 may allow a radiation oncologist to view and manipulate treatment planning CT scans (e.g., based on image data 103), treatment planning tools, dosage displays, treatment dosages, dose prescriptions, and dose volume histograms (DVH), for example. Shared EP and RO workspace computing device 108 may allow an electrophysiologist to view and manipulate meshes, such as 3D meshes, of structures (e.g., heart substructures) and dose volumes.

In some examples, each of EP workspace computing device 104, RO workspace computing device 106, and shared EP and RO workspace computing device 108 execute a respective application, where each application is tailored (e.g., customized) to the expectations of the corresponding medical professional. For example, RO workspace computing device 106 may execute an RO application tailored toward the expectations and tasks of a radiation oncologist. EP workspace computing device 104 may execute an EP application tailored toward the expectations and tasks of an electrophysiologist, and shared EP and RO workspace computing device 108 may execute one or more applications tailored toward the expectations of one or both of the electrophysiologist and radiation oncologist.

In some examples, in response to an input from an electrophysiologist, EP workspace computing device 104 performs an action. In addition, in response to the input, EP workspace computing device 104 may generate EP adjustment data 105 identifying and characterizing the action, and may transmit the EP adjustment data 105 to RO workspace computing device 106. In response to receiving EP adjustment data 105, RO workspace computing device 106 may perform another action.

For example, an electrophysiologist may provide an input to EP workspace computing device 104 (e.g., via input/output device 203) and in response, EP workspace computing device 104 may align a segmentation model, such as a 17 segment model, to an organ's structure, such as to a heart's ventricle. EP workspace computing device 104 may further generate EP adjustment data 105 identifying and characterizing the alignment, and may transmit EP adjustment data 105 to RO workspace computing device 106. In response to receiving EP adjustment data 105, to RO workspace computing device 106 may display the 17 segments in a planning CT image. As a result, a radiation oncologist operating RO workspace computing device 106 may view the displayed 17 segments in the planning CT image. Alternatively, EP workspace computing device 104 may transmit the EP adjustment data 105 to shared EP and RO workspace computing device 108. In response to receiving EP adjustment data 105, shared EP and RO workspace computing device 108 may display the 17 segments in a planning CT image, for example.

As another example, an electrophysiologist may provide an input to EP workspace computing device 104 (e.g., via input/output device 203), and in response, EP workspace computing device 104 may create a target (e.g., target area of a structure). EP workspace computing device 104 may generate EP adjustment data 105 identifying and characterizing the target, and may further transmit generate EP adjustment data 105 to RO workspace computing device 106. In response, RO workspace computing device 106 may generate an image (e.g., a 3D volume) of the target, and may display the image of the target to, for example, the radiation oncologist. Alternatively, EP workspace computing device 104 may generate EP adjustment data 105 identifying and characterizing the target, and may further transmit generate EP adjustment data 105 to shared EP and RO workspace computing device 108. In response, shared EP and RO workspace computing device 108 may generate an image (e.g., a 3D volume) of the target, and may display the image of the target to, for example, the radiation oncologist.

Moreover, in some examples, the electrophysiologist may provide a second input to EP workspace computing device 104 to edit the target. In response to the second input, EP workspace computing device 104 may edit the target in accordance with the second input. EP workspace computing device 104 may generate EP adjustment data 105 identifying and characterizing the edit to the target, and may further transmit generate EP adjustment data 105 to RO workspace computing device 106. In response, RO workspace computing device 106 may edit the image of the target according to the edit to the target identified by EP adjustment data 105, and may display the edited image to the radiation oncologist. Alternatively, shared EP and RO workspace computing device 108 may receive the EP adjustment data 105, and the radiation oncologist may edit the target in accordance with edits identified by EP adjustment data 105.

In some examples, the radiation oncologist may provide an input to the RO workspace computing device 106. In response, RO workspace computing device 106 performs an action. Further, RO workspace computing device 106 may generate RO adjustment data 107 identifying and characterizing the action, and may transmit the RO adjustment data 107 to EP workspace computing device 104. In response to receiving RO adjustment data 107, EP workspace computing device 104 may perform another action.

As an example, and continuing the example from above, the radiation oncologist may provide an input to the RO workspace computing device 106 to provide a second edit to the displayed target. In response, RO workspace computing device 106 may edit the displayed target in accordance with the input. In addition, RO workspace computing device 106 may generate RO adjustment data 107 identifying and characterizing the second edit, and may transmit the RO adjustment data 107 to EP workspace computing device 102. EP workspace computing device 102 may receive the RO adjustment data 107, and may edit the target in accordance with the second edit as identified by the RO adjustment data 107. Alternatively, shared EP and RO workspace computing device 108 may receive the RO adjustment data 107, and the electrophysiologist may edit the target in accordance with edits identified by RO adjustment data 107.

As such, the embodiments described herein may allow various medical professionals, such as an electrophysiologist and a radiation oncologist, to more efficiently collaborate during the generation of a treatment plan. For example, the embodiments may allow for real-time communications between the EP workspace computing device 104 and the RO workspace computing device 106. Further, the communications allow for edits (e.g., changes, updates) on one medical professional's workspace (e.g., the electrophysiologist workspace on the EP workspace computing device 104) that are based on edits performed by another medical provisional on another workspace (e.g., the radiation oncologist's workspace on the RO workspace computing device 106). Alternatively, the communications allow for edits (e.g., changes, updates) on one medical professional's workspace (e.g., the electrophysiologist workspace on the EP workspace computing device 104) that are based on edits performed by another medical provisional on another workspace (e.g., the radiation oncologist's workspace on the RO workspace computing device 106) and are received by the shared EP and RO workspace to collaborate in the shared EP and RO workspace.

Figure 3:
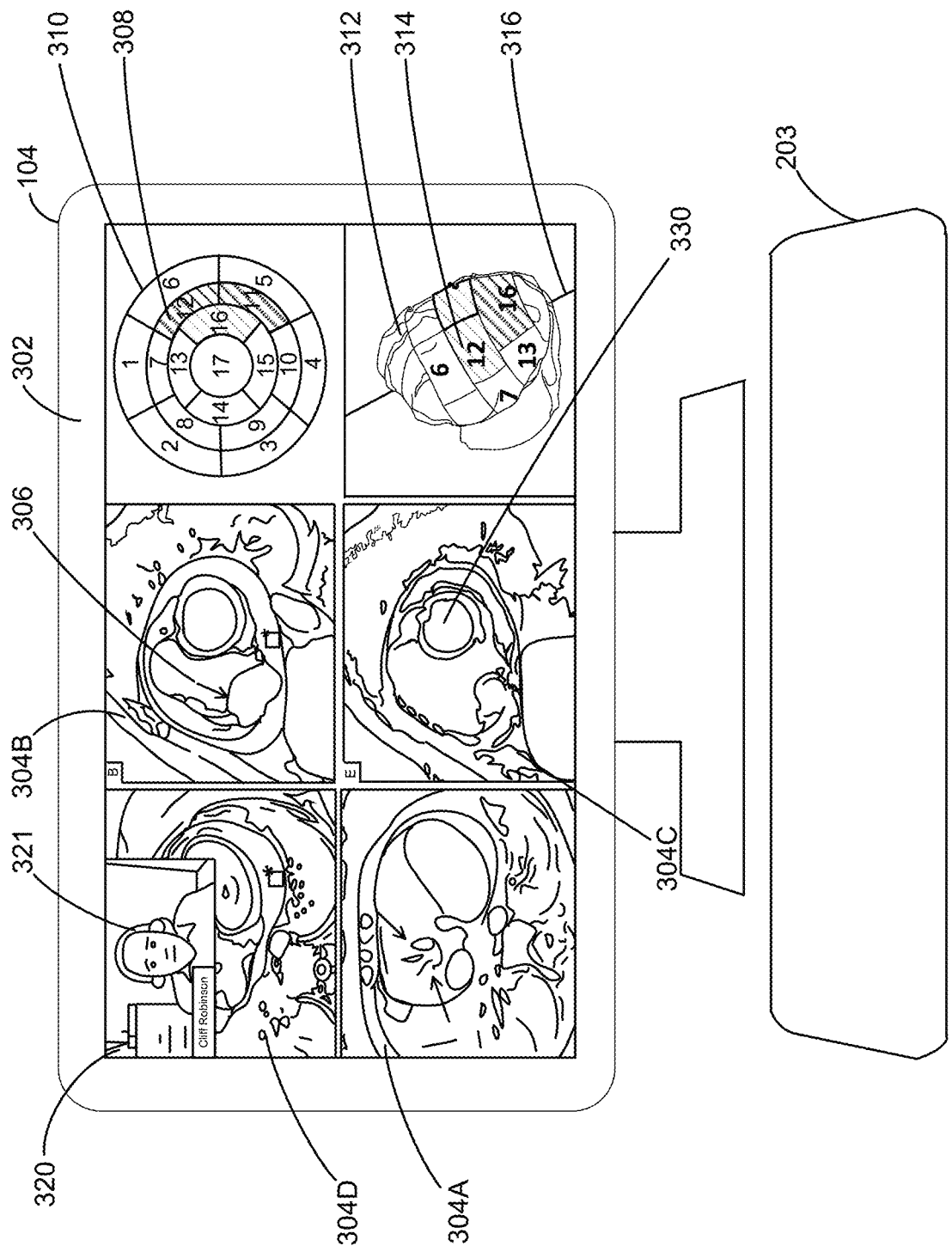
FIG. 3 illustrates an electrophysiologist (EP) workspace provided by an EP workspace computing device, in accordance with some embodiments.

FIG. 3 illustrates an EP workspace 302 provided by EP workspace computing device 104. EP workspace computing device 104 includes an input/output device 203, such as a keyboard, to allow a user, such as an electrophysiologist, to provide input. EP workspace computing device 104 may display EP workspace 302 in response to executing an application, such as an application tailored to an electrophysiologist, for example.

In this example, EP workspace 302 displays various ablation volume images 304A, 304B, 304C, 304D. The various ablation volume images 304A, 304B, 304C, 304D may have been captured by imaging device 102, for example. In some examples, EP workspace computing device 104 allows the electrophysiologist to identify an area of an ablation volume image 304A with one or more identification icons 306. EP workspace 302 further displays a segmentation model 310 of an organ (in this example, a 17 segment model of a heart ventricle) and a 3D image 312 of the organ.

Figure 4:
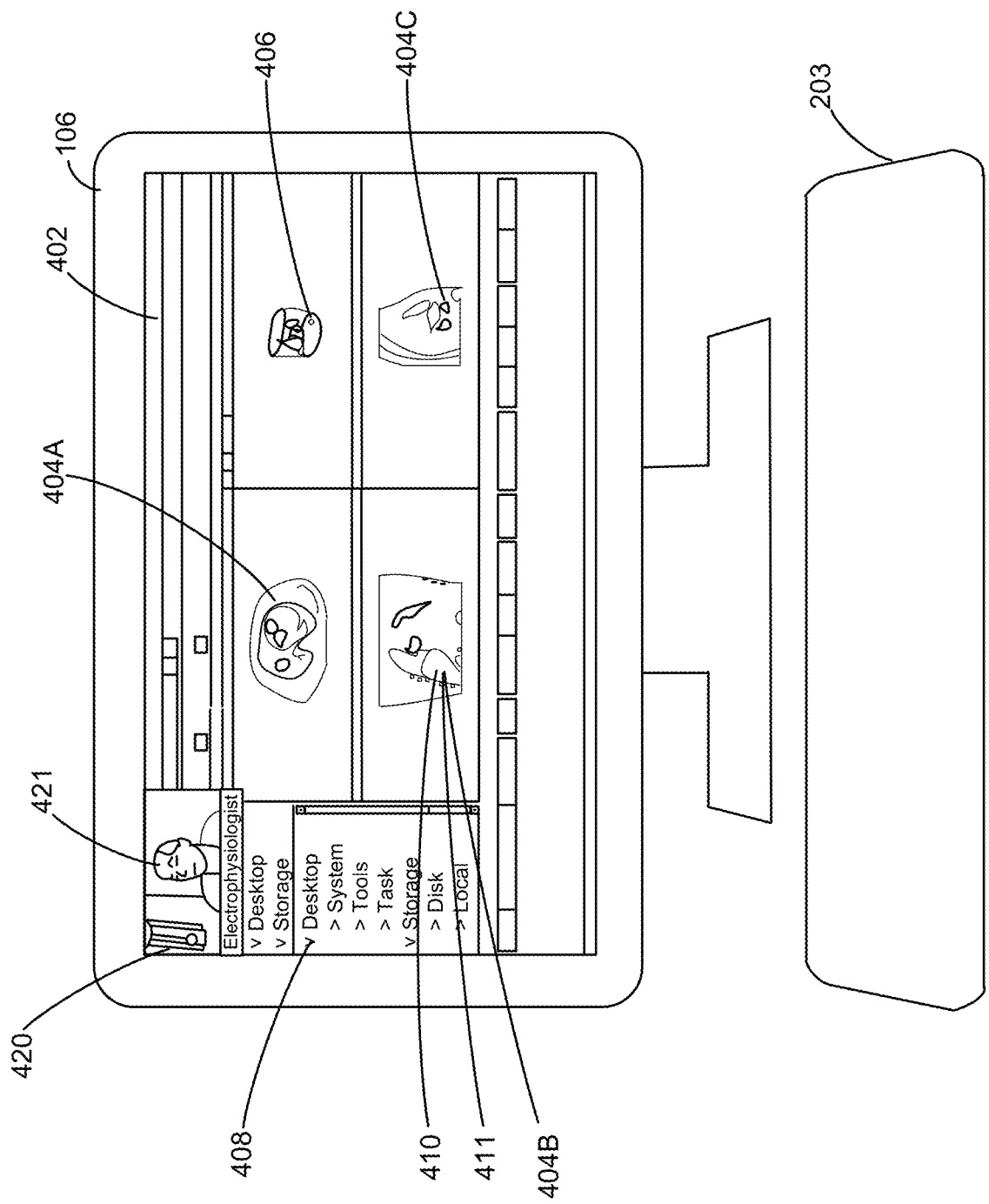
FIG. 4 illustrates a radiation oncologist (RO) workspace provided by an RP workspace computing device, in accordance with some embodiments.

FIG. 4 illustrates an RO workspace 402 provided by RO workspace computing device 106. RO workspace computing device 106 includes an input/output device 203, such as a keyboard, to allow a user, such as a radiation oncologist, to provide input. RO workspace computing device 106 may display RO workspace 402 in response to executing an application, such as an application tailored to a radiation oncologist, for example. In this example, RO workspace 402 displays various image scans 404A, 404B, 404C, as well as a 3D substructure mesh 406. Image scan 404A may be a scan taken from the top of a person (e.g., looking down onto the head of the person). Image scan 404B may be a scan take from a front view of the person. Image scan 404C may be a scan taken from a side (e.g., right side) of the person. RO workspace 402 further displays a menu window 408 that allows for the selection, and thus the display, of images.

Referring back to FIG. 3, EP workspace 302 allows the electrophysiologist to select one or more regions 308 of the segmentation model 310. In some examples, EP workspace 302 changes a color of a selected region 308 to indicate the selection. In response to selecting a region 308, EP workspace computing device 104 may generate EP adjustment data 105 identifying and characterizing the selected region 308. EP workspace computing device 104 may transmit the EP adjustment data 105 to RO workspace computing device 106.

In some examples, EP workspace 302 includes drawing tools that allow the electrophysiologist to identify (e.g., define) an area of a structure 330 displayed within ablation volume image 304B. The area of the structure 330 may be one that the electrophysiologist wants to identify for radioablation, or to protect from radioablation, for example. In response to identifying the area of the structure 330, EP workspace computing device 104 may generate EP adjustment data 105 identifying and characterizing the identified area of the structure. EP workspace computing device 104 may transmit the EP adjustment data 105 to RO workspace computing device 106.

For example, EP workspace 302 may provide an icon, such as a "SEND" icon, that, if selected (e.g., clicked), may cause EP workspace computing device 104 to transmit the EP adjustment data 105 to RO workspace computing device 106. In some examples, a menu (e.g., a drop-down menu) allows the electrophysiologist to select one or more RO workspace computing devices 106. In response, EP workspace 302 may transmit the EP adjustment data 105 to the selected RO workspace computing devices 106.

With reference to FIG. 4, in response to receiving EP adjustment data 105, RO workspace computing device 106 may identify a corresponding portion 411 of an organ 410 in an image scan 404B. RO workspace computing device 106 may apply one or more algorithms to determine the corresponding portion 411 of the organ 410. RO workspace computing device 106 may identify the corresponding portion 411 of the organ 410 by highlighting a perimeter of the corresponding portion 411 of the organ 410, for example. As such, the radiation oncologist may easily see the area identified (e.g., targeted) by the electrophysiologist operating the EP workspace computing device 104.

Referring back to FIG. 3, and further in response to selecting a region 308, EP workspace 302 may automatically edit (e.g., update) the 3D image 312. For example, EP workspace 302 may change the color of a corresponding portion 314 of the 3D image 312 based on the selected region 308. EP workspace 302 may further allow the electrophysiologist to rotate the 3D image 312. For example, the electrophysiologist may rotate the 3D image 312 about a longitudinal axis 316 where the 3D image 312 is updated according to the rotation.

With reference to FIG. 4, RO workspace 402 may include drawing tools that allow a radiation oncologist to select a portion 411 of an organ 410 in an image scan 404B. In some examples, workspace 402 highlights the selected portion 411. In response to selecting the portion 411, RO workspace 402 may generate RO adjustment data 107 identifying and characterizing the selected portion 411. RO workspace computing device 106 may transmit the RO adjustment data 107 to EP workspace computing device 104. For example, RO workspace 402 may provide an icon, such as a "SEND" icon, that, if selected (e.g., clicked), may cause RO workspace computing device 106 to transmit the RO adjustment data 107 to EP workspace computing device 104. In some examples, a menu (e.g., a drop-down menu) allows the radiation oncologist to select one or more EP workspace computing devices 104. In response, RO workspace 402 may transmit the RO adjustment data 107 to the selected EP workspace computing devices 104.

With reference to FIG. 3, in response to receiving RO adjustment data 107, EP workspace computing device 104 may identify a corresponding portion 314 of the 3D image 312. EP workspace computing device 104 may apply one or more algorithms to determine the corresponding portion 314 of the 3D image 312. EP workspace computing device 104 may identify the corresponding portion 314 of the 3D image 312 by highlighting the portion in a different (e.g., and configurable) color, for example. As such, the electrophysiologist may easily see the area identified (e.g., targeted) by the radiation oncologist operating the RO workspace computing device 106.

In addition, in some examples, EP workspace computing device 104 and RO workspace computing device 106 may provide for audio and/or video communications between the electrophysiologist and the radiation oncologist. For example, and with reference to FIG. 3, EP workspace 302 may include a communication window 320 that displays video of a radiation oncologist 321 operating RO workspace computing device 106. Audio received from RO workspace computing device 106 may be provided over one or more speakers of EP workspace computing device 104.

Similarly, and with reference to FIG. 4, RO workspace computing device 106 may include a communication window 420 that displays video of an electrophysiologist 421 operating EP workspace computing device 104. Audio received from EP workspace computing device 104 may be provided over one or more speakers of RO workspace computing device 106. Communication windows 320 and 420 may, in some examples, provide a messaging (e.g., chat) capability, where the radiation oncologist 321 and the electrophysiologist 421 may exchange messages.

In some examples, communication windows 320 and 420 allow for the sharing (e.g., transmission and receiving) of notes, status (e.g., volume status, approval status, treatment plan status (e.g., complete, in process, etc.)), or any other relevant information. In addition, in some examples, EP workspace computing device 104 and/or RO workspace computing device 106 may store any of this information in database 116.

Although various examples of generating and transmitting data from one of EP workspace computing device 104 and RO workspace computing device 106 to another to cause actions to be taken by the receiver of the data are illustrated, those of ordinary skill in the art having the benefit of these disclosures would appreciate other examples as well. For example, EP workspace computing device 104 may generate EP adjustment data 105 that identifies and characterizes any action taken on EP workspace 302, and RO workspace computing device 106 may take any suitable action in response to receiving EP adjustment data 105. Similarly, RO workspace computing device 106 may generate RO adjustment data 107 that identifies and characterizes any action taken on RO workspace 402, and EP workspace computing device 104 may take any suitable action in response to receiving RP adjustment data 107.

Figure 5A:
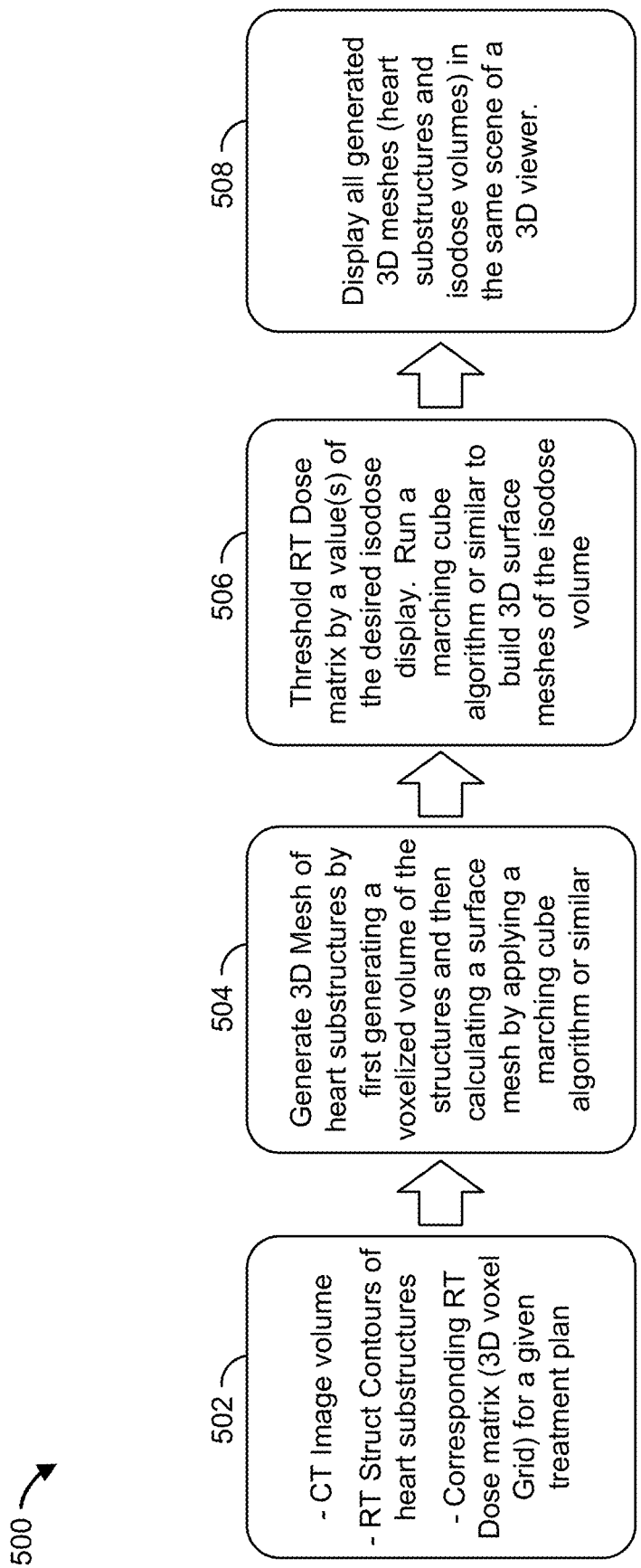
FIG. 5A illustrates a method for generating a concurrent display of structure and dose volume meshes, in accordance with some embodiments.
Figure 5B:
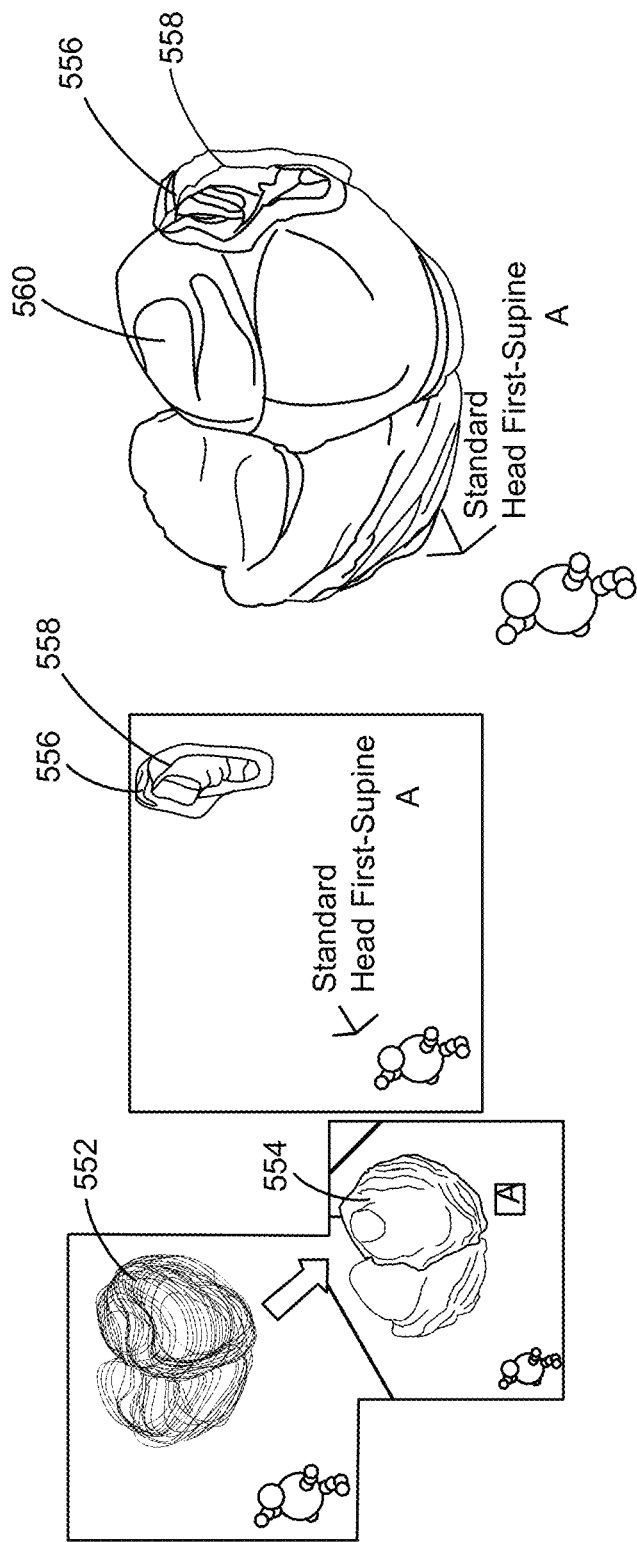
FIG. 5B illustrates the display of meshes according to the method of FIG. 5A, in accordance with some embodiments.

FIG. 5A illustrates a method 500 for generating a concurrent display of structure and dose volume meshes, and FIG. 5B illustrates corresponding diagrams. Method 500 may be performed by a computing device, such as shared EP and RO workspace computing device 108. Shared EP and RO workspace computing device 108 may present information, such as location, size, shape, and intensity of a dose region to be applied to a structure, to a referring electrophysiologist, for example. The information may be presented in a way that the referring electrophysiologist is familiar or comfortable with.

Beginning at step 502, input data is received. Input data may include, for example, a CT image volume, radiotherapy (RT) structure contours of organ substructures, in this example heart substructures, and dose matrix data identifying corresponding RT dose matrices (e.g., as a 3D voxel grid) for a given treatment plan. In some examples, at least a portion of the input data is obtained from database 116. In some examples, the CI image volume is received from imaging device 102. In some examples, the dose matrix data is received from RO computing device 106. For example, a radiation oncologist may determine a dose prescription (e.g., an amount of dose and organ location for the dose) for the treatment plan. The radiation oncologist may provide the dose prescription (e.g., via user interface 205) to RO computing device 106. A physicist or dosimetrist may develop a treatment plan to satisfy (e.g., based on) the dose prescription (e.g., via RO computing device 106 or shared EP and RO workspace computing device 108). The treatment plan may include the generation of a planning image. Each of the dose prescription, the treatment plan, and the planning image may be stored in database 116, for example. RO computing device 106 may generate the dose matrix based on the developed treatment plan and/or planning image. For example, RO computing device 106 may execute one or more dose matrix algorithms as known in the art to generate dose matrix data identifying and characterizing the dose matrix. RO computing device 106 may store the dose matrix data in database 116.

At step 504, heart substructure 3D meshes 554 are generated. The heart substructure 3D meshes 554 may be generated, for example, by generating a voxelized volume of the heart substructures and then determining (e.g., calculating) a substructure surface mesh 552 based on the voxelized volume of the heart substructures. For example, shared EP and RO workspace computing device 108 may execute an image based meshing algorithm that operates on the voxelized volume of the heart substructures to determine the substructure surface mesh 552. The image based meshing algorithm may be, for example, a Marching Cube algorithm, a Marching Tetrahedra algorithm, or a Neighboring Cell algorithm, for example.

Proceeding to step 506, a threshold is applied to each RT dose matrix (as identified in the received dose matrix data) to generate an isodose volume 558. The threshold is based on a value (e.g., selectable by a electrophysiologist as provided on a configuration menu) for a desired isodose display. For example, the isodose volume 558 may include areas where the dose is above the threshold. An isodose 3D surface mesh 556 is then generated based on the isodose volume 558. For example, shared EP and RO workspace computing device 108 may execute an image based meshing algorithm that operates on the isodose volume 558 to generate the isodose 3D surface mesh 556. In some examples, multiple isodose 3D surface meshes 556 are generated, each isodose 3D surface mesh 556 based on a corresponding threshold. For example, one isodose 3D surface mesh 556 may be generated based on a 10 Gray (Gy) threshold, and another isodose 3D surface mesh 556 may be generated based on a 25 Gy threshold.

At step 508, the generated 3D meshes, including the heart substructure 3D meshes 554 and the isodose 3D surface mesh 556, are displayed as one image (e.g., are displayed together). For example, the heart substructure 3D meshes 554 and the isodose 3D surface mesh 556 may be displayed within the same scene of a 3D viewer or workspace. The isodose 3D surface mesh 556 is displayed such that it appears within a corresponding portion of the heart substructure 3D meshes 554. For example, the isodose 3D surface mesh 556 may be laid over the corresponding portion of the heart substructure 3D meshes 554 that will receive dosage. In some examples, shared EP and RO workspace computing device 108, via an EP workspace, allows for the moving and/or rotating of the output image 560. In some examples, the electrophysiologist may be able to control a position and direction of a camera of imaging device 102, remotely from shared EP and RO workspace computing device 108, to provide image data 103 from various angles.

Figure 6A:
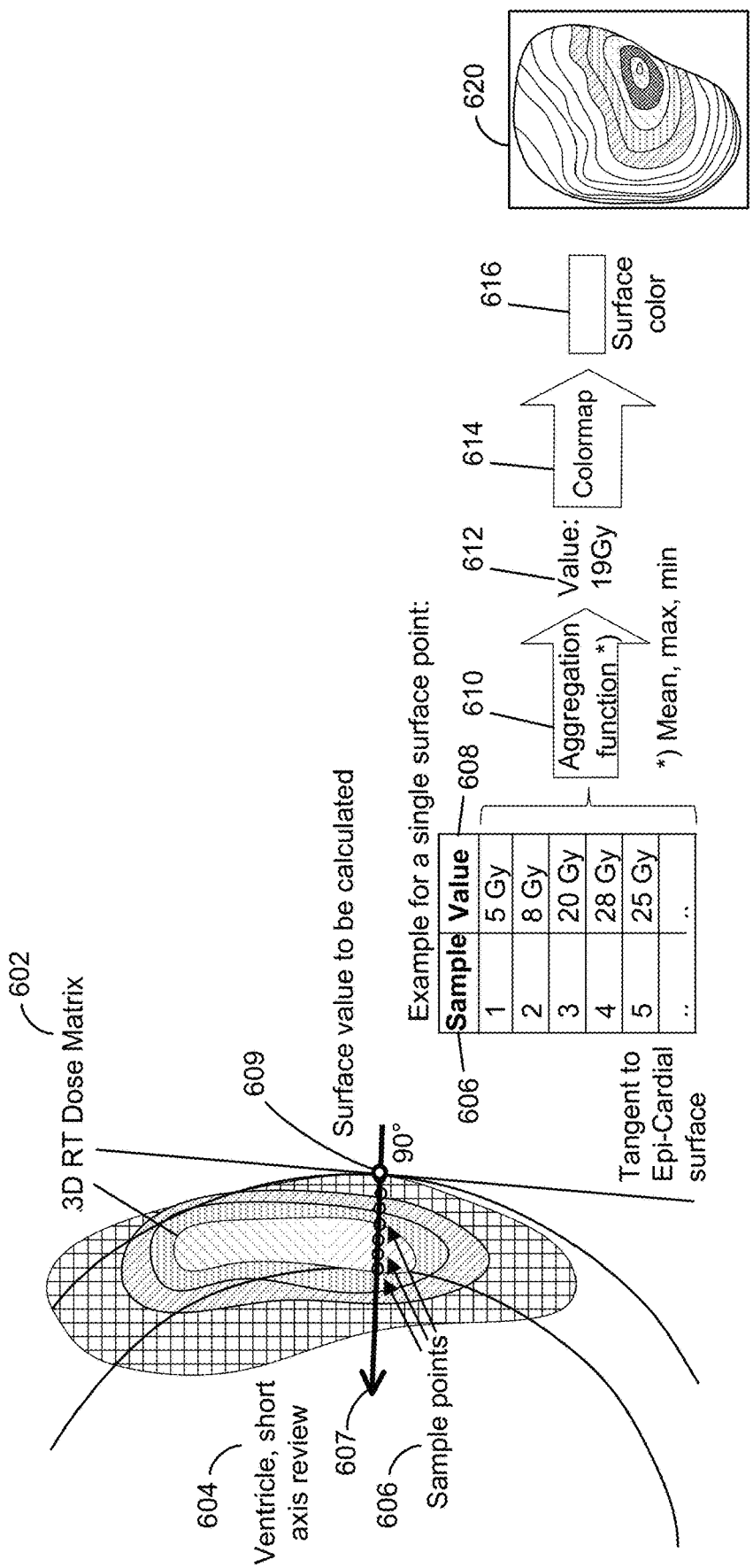
FIG. 6A illustrates the determination of surface color for a substructure, in accordance with some embodiments.

FIG. 6A illustrates a 3D RT dose matrix 602 for a heart ventricle 604. Sample points 606 are determined along a line 607 perpendicular to a tangential point 609 along an area of the 3D RT dose matrix 602 defined by the contours of the organ structure. For example, shared EP and RO workspace computing device 108 may select a number of sample points 606 along each of a plurality of lines 607 that are tangential to the area of the 3D RT dose matrix 602 defined by the contours of the organ structure. The number of sample points 606, and the distance between the sample points 606, may be configured by a user, such as an electrophysiologist operating shared EP and RO workspace computing device 108.

Each sample point 606 has a corresponding value 608. The values 608 may indicate, for example, an amount of dosage at a location of the 3D RT dose matrix 602 corresponding to each sample point 606. Shared EP and RO workspace computing device 108 may execute an aggregation function 610 to determine a representative value 612 based on the corresponding values 608 to the sample points 606. For example, the representative value 612 may be a mean of the values 608, a maximum of the values 608, or a minimum of the values 608. In some examples, shared EP and RO workspace computing device 108 executes any suitable aggregation function 610 that determines a representative value 612 based on the values 608.

Based on a color map 614 that associates colors to representative values 612, shared EP and RO workspace computing device 108 may determine surface colors 616 of a substructure, such as ventricle 604. For example, shared EP and RO workspace computing device 108 may generate a mesh based on output image 560 that includes the various colors on its surface, such as is illustrated with substructure surface 620.

Figure 6B:
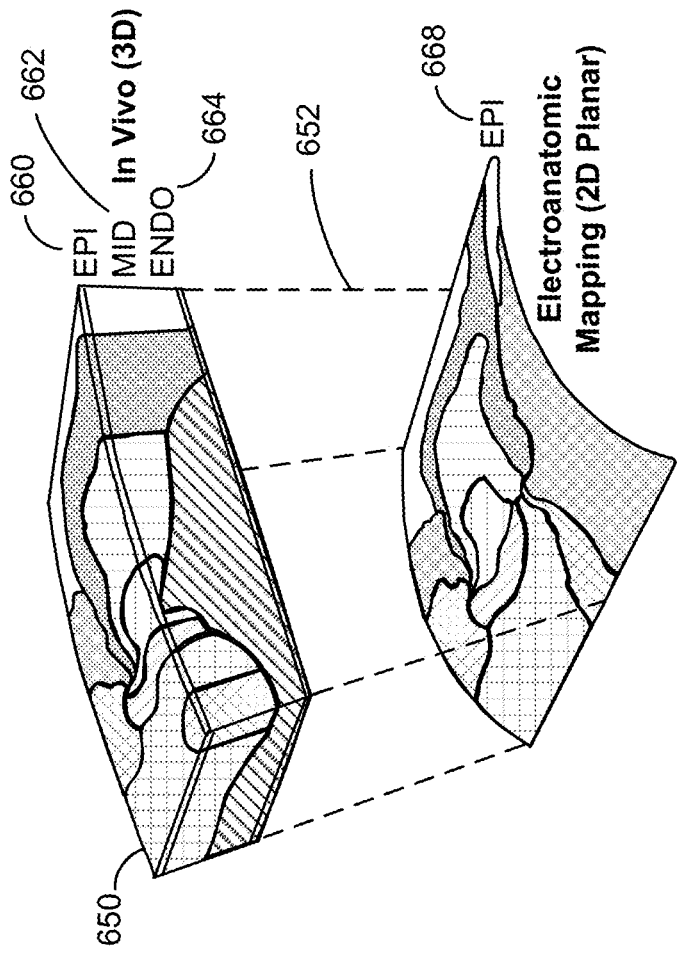
FIG. 6B illustrates a three dimensional image of a substructure with surface color, in accordance with some embodiments.

FIG. 6B illustrates a 3D image 650 of a substructure with surface color. For example, shared EP and RO workspace computing device 108 may have determined and generated the surface color as described herein, such as with respect to FIG. 6A. In this example, the 3D image 650 is of a ventricle 652 and, more specifically, a 3D image of a ventricular tachycardia circuit of a portion of ventricle 652. The various colors on various surfaces may indicate varying dosage levels on those surfaces. For example, as illustrated, ventricle 652 includes a first epicardial surface 660, a second epicardial surface 668, a myocardium surface 662, and an endocardial surface 664. Each of the first epicardial surface 660, the second epicardial surface 668, the myocardium surface 662, and the endocardial surface 664 display colors based on the dosage along those respective surfaces. As such, the dose distribution inside each of the segments of ventricle 652 (e.g., epicardial, myocardium, and endocardial segments) is projected to an inner or outer surface such that each point on the surface indicates the dose received at that particular location. As such, the dosage information is provided to an electrophysiologist in a manner that facilitates an easier understanding and appreciation of the various surfaces of a structure receiving the dosage, as well as relative amounts of the dosage.

Figure 7:
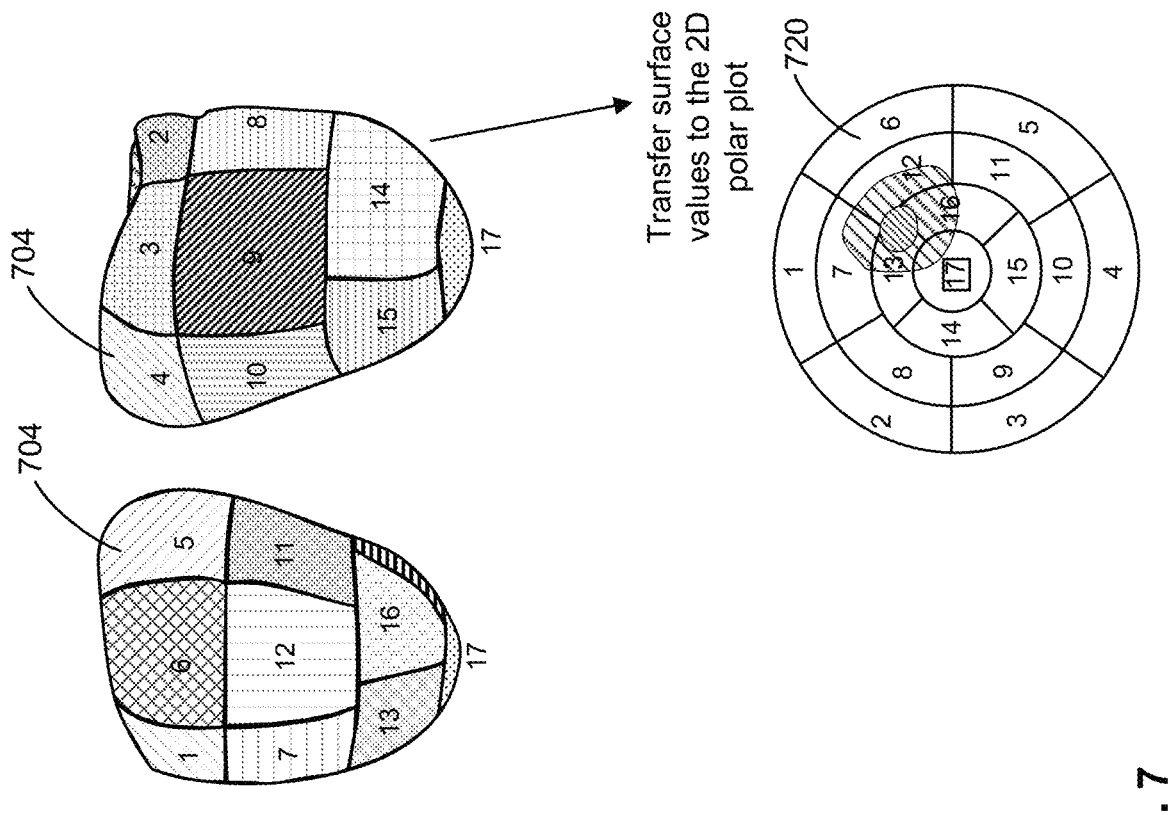
FIG. 7 illustrates the mapping of a three dimensional surface mesh to a segment model, in accordance with some embodiment.
Figure 7:
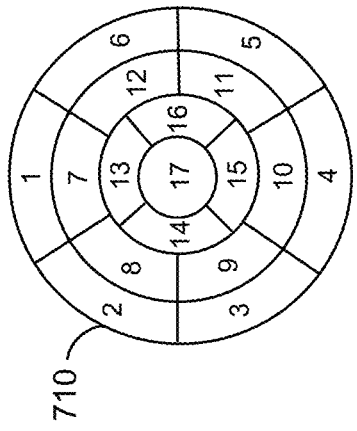
Figure 7:
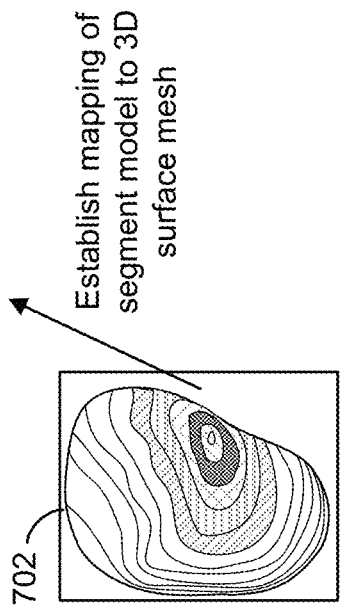

FIG. 7 illustrates an example where determined surface dose values representing dosage along sample points of a surface of a myocardium are projected onto a 17 segment model of a ventricle, thereby allowing for the display of dosage on a 2D map of the ventricle.

In this example, a colored substructure model 702 is mapped to a 3D surface mesh 704, such that the 3D surface mesh 704 is displayed with corresponding colors. The colors of the surfaces of colored substructure model 702 may be determined as described herein, such as with respect to FIG. 6A (e.g., as described with respect to substructure surface 620). In some examples, the dose values representing dosage are projected to an endocardial wall (i.e., inner layer of the myocardium) rather than an epicardial wall (i.e., outer layer of the myocardium), for example.

Shared EP and RO workspace computing device 108 may further identify portions of 3D surface mesh 704 corresponding to a 17 segment model, such as 17 segment model 710. Based on the identified portions of 3D surface mesh 704 and the colors of the various portions of the colored substructure model 702, shared EP and RO workspace computing device 108 may generate a colored 17 segment display.

For example, for each segment of 17 segment display 720 (e.g., before its displayed with colors), shared EP and RO workspace computing device 108 may determine a corresponding portion in the 3D surface mesh 704. shared EP and RO workspace computing device 108 may then identify the segment number of the portion in the 3D surface mesh 704 and, based on the segment number, determine the color (e.g., a value) of a corresponding portion of the colored substructure model 702. Shared EP and RO workspace computing device 108 may then associate the segment of the 17 segment display 720 with the same color as that of the corresponding portion of the colored substructure model 702. In some examples, shared EP and RO workspace computing device 108 generates (e.g., calculates) segment specific dose volume histograms (DVHs), and stores them in a database, such as database 116.

With reference to FIGS. 6A, 6B, and 7, although various colors are used to generate images indicating dosage levels, other ways of providing (e.g., displaying) the dosage information are also contemplated. For example, rather than using colors, other dosage level identifiers may be used, such as color wash overlays, translucent overlays, shading, hashing, or any other suitable techniques. The dose information, for example, may assist an electrophysiologist in evaluating whether a planned ablation volume is as intended for treatment. For example, the dose information may assist the electrophysiologist in identifying whether a calculated treatment plan results in an appropriate dose coverage of an intended ablation location and/or volume.

Figure 8A:
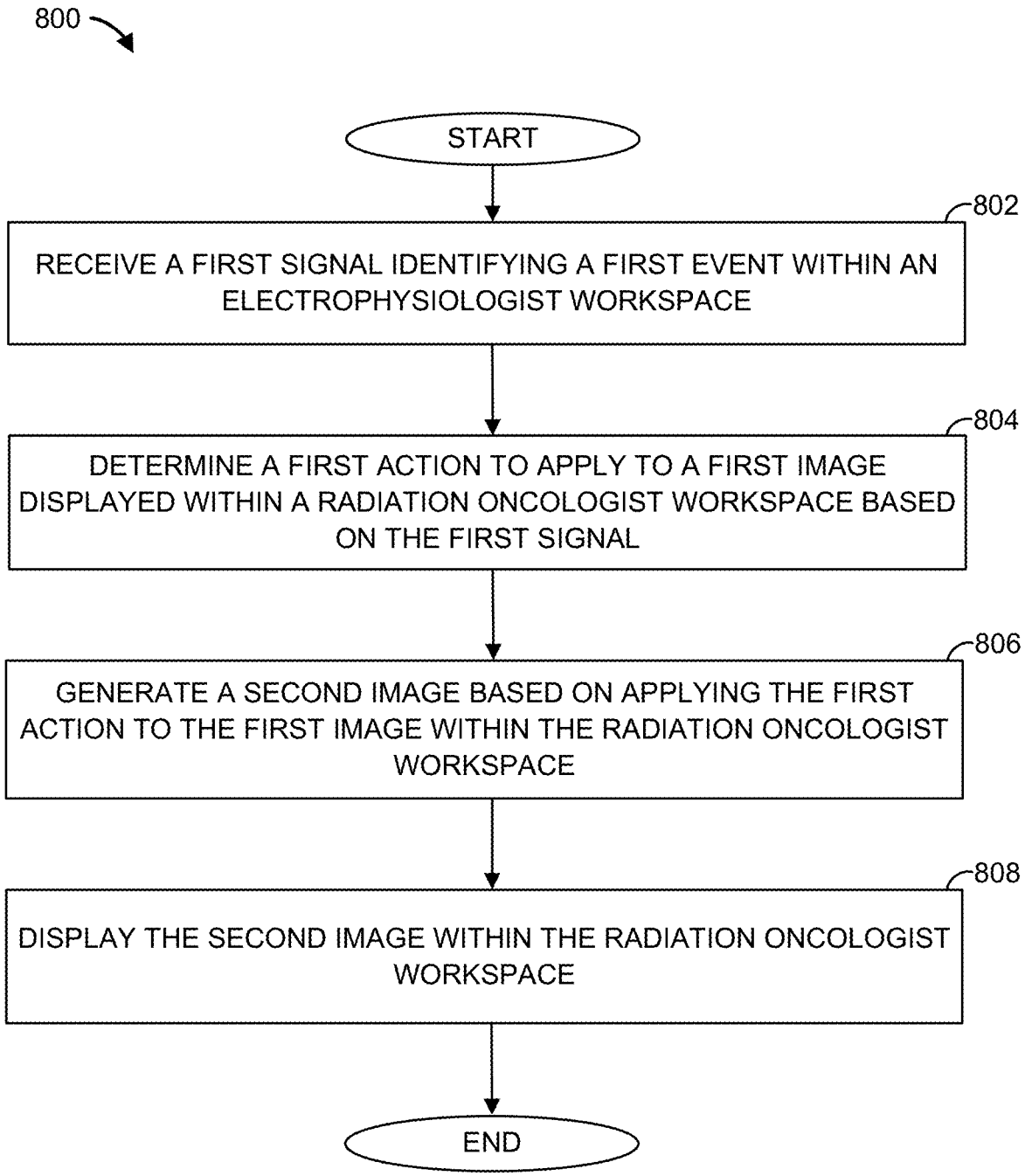
FIG. 8A is a flowchart of an example method to display an image within the RO workspace of FIG. 4, in accordance with some embodiments.

FIG. 8A is a flowchart of an example method 800 that can be carried out by, for example, RO workspace computing device 106. Beginning at step 802, a first signal is received. The first signal identifies a first event within an electrophysiologist workspace. For example, RO workspace computing device 106 may receive from EP workspace computing device 104 EP adjustment data 105 identifying and characterizing the selection of one or more segments of a segment model, such as a 17 segment model, to a ventricle. At step 804, a first action to apply to a first image displayed within an RO workspace is determined based on the first signal. For example, RO workspace 402 may display a first 3D image of a heart of a patient. The first action may be, for example, the determination of one or more portions of the heart corresponding to the selected areas.

At step 806, a second image is generated based on applying the first action to the first image within the RO workspace. For example, RO workspace computing device 106 may generate a second 3D image of the heart of the patient with the determined portions identified (e.g., highlighted, outlined, colored, etc.). RO workspace computing device 106 may display the second 3D image within RO workspace 402. At step 808, the second image is displayed within the RO workspace. In some examples, RO workspace computing device 106 generates a cardiac radioablation treatment plan based on the second image. In some examples, RO workspace computing device 106 transmits the cardiac radioablation treatment plan to a radiotherapy delivery system to deliver the dosage to a patient. The method then ends.

Figure 8B:
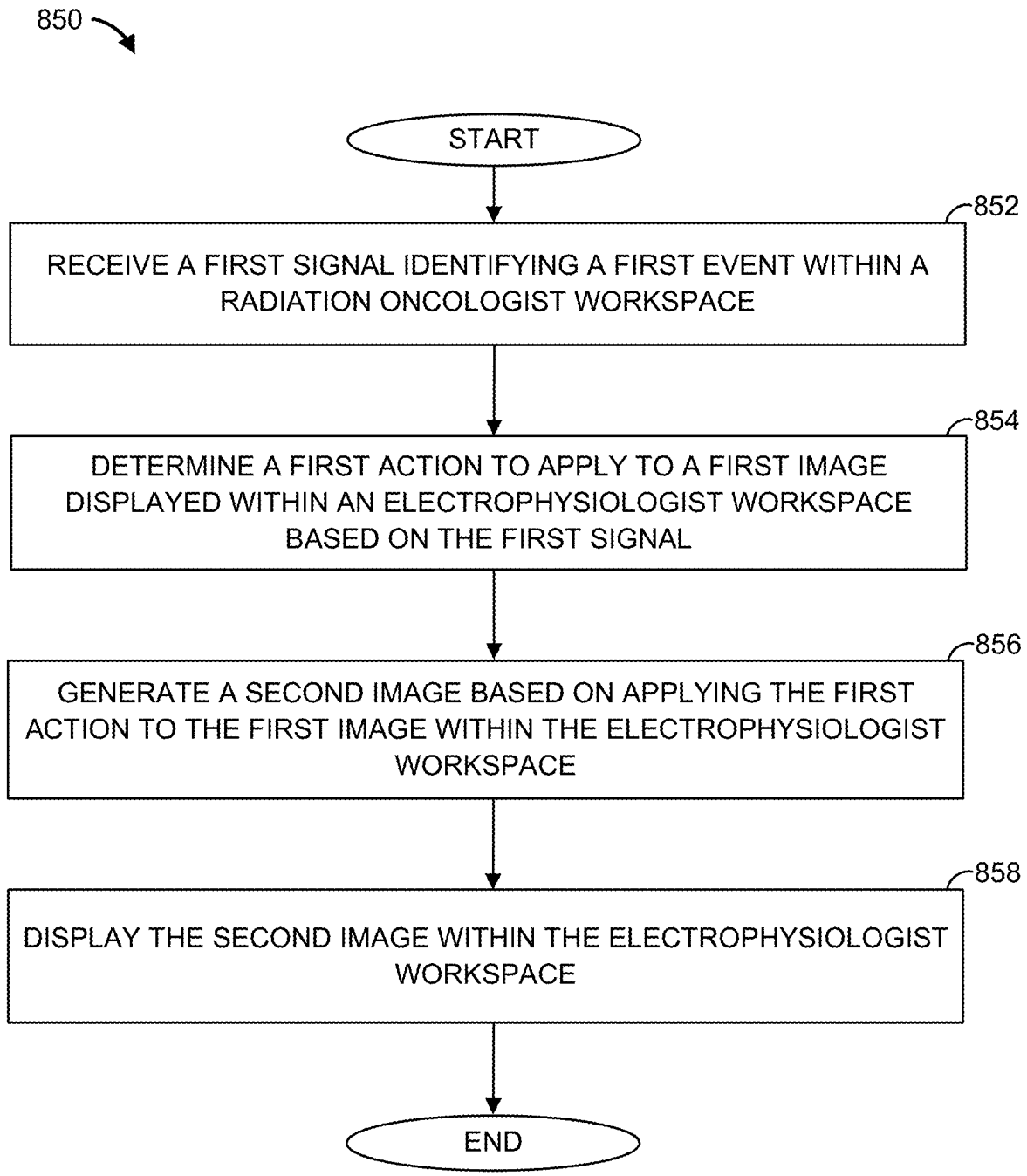
FIG. 8B is a flowchart of an example method to display an image within the EP workspace of FIG. 3, in accordance with some embodiments.

FIG. 8B is a flowchart of an example method 850 that can be carried out by, for example, EP workspace computing device 104. Beginning at step 852, a first signal is received. The first signal identifies a first event within a radiation oncologist workspace. For example, EP workspace computing device 104 may receive from RO workspace computing device 106 RO adjustment data 107 identifying and characterizing a change to a dosage to apply to a ventricle. At step 854, a first action to apply to a first image displayed within an EP workspace is determined based on the first signal. For example, EP workspace 302 may display a first 3D image of the ventricle. The first action may be, for example, the determination of a portion of the ventricle to which the changed dosage is to be applied.

At step 856, a second image is generated based on applying the first action to the first image within the EP workspace. For example, EP workspace computing device 104 may generate a second 3D image of the ventricle in one color, but with the portions of the ventricle with dosage in a different color. EP workspace computing device 104 may display the second 3D image within EP workspace 302. At step 858, the second image is displayed within the EP workspace. In some examples, EP workspace computing device 104 generates a cardiac radioablation treatment plan based on the second image. In some examples, EP workspace computing device 104 transmits the cardiac radioablation treatment plan to a radiotherapy delivery system to deliver the dosage to a patient. The method then ends.

Figure 9:
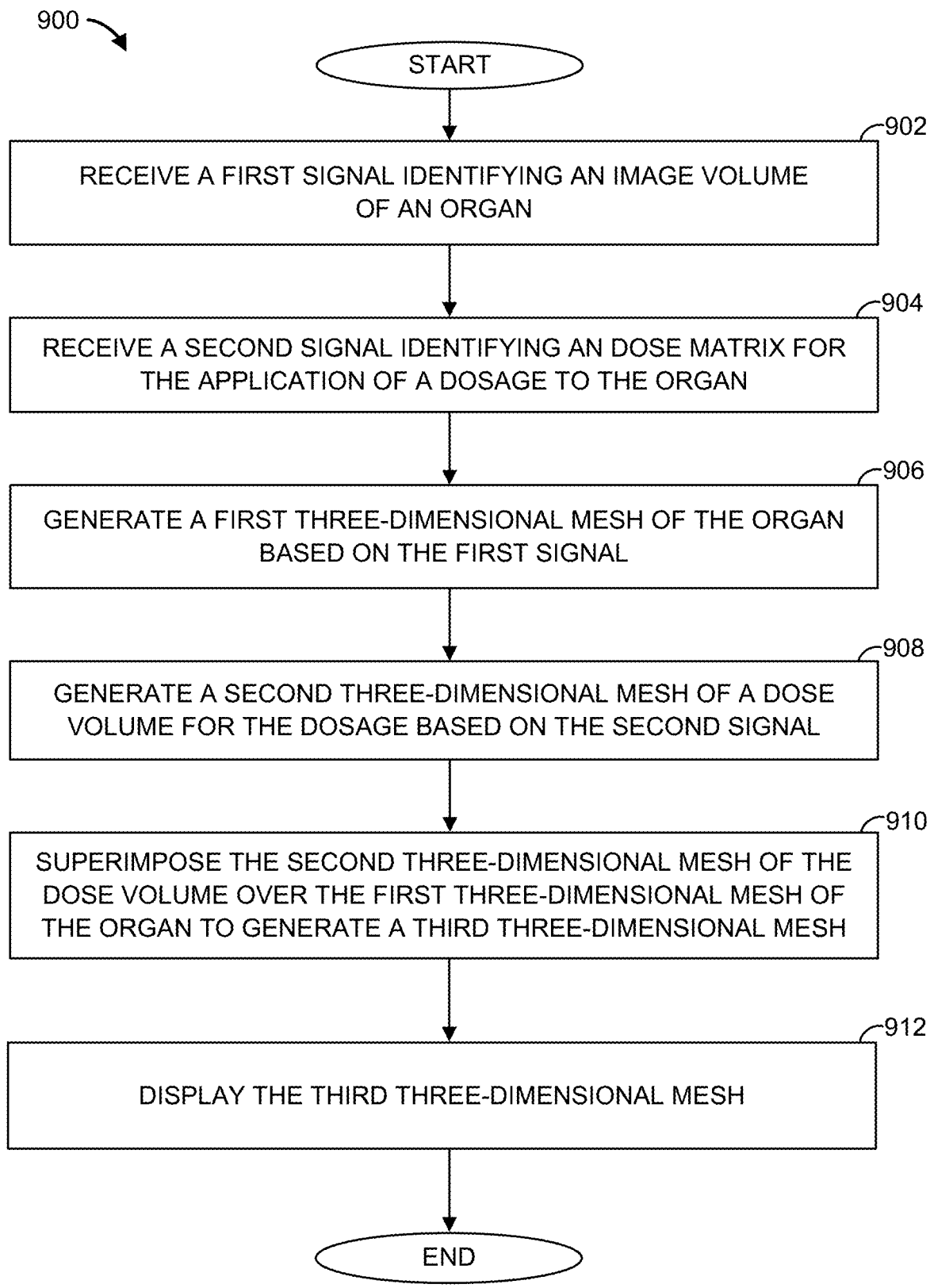
FIG. 9 is a flowchart of an example method to display a three dimensional mesh, in accordance with some embodiments.

FIG. 9 is a flowchart of an example method 900 that can be carried out by, for example, shared EP and RO workspace computing device 108. Beginning at step 902, a first signal identifying an image volume of an organ is received. For example, shared EP and RO workspace computing device 108 may receive from imaging device 102 image data 103, which identifies and characterizes a CT image volume. At step 904, a second signal is received. The second signal identifies dose matrix data for the application of a dosage to the organ. For example, shared EP and RO workspace computing device 108 may receive the dose matrix data from RO computing device 106.

Proceeding to step 906, a first three-dimensional mesh of the organ is generated based on the first signal. For example, shared EP and RO workspace computing device 108 may execute one or more algorithms that operate on at least portions of the received image volume to generate the first three-dimensional mesh of the organ. In some examples, shared EP and RO workspace computing device 108 calculates the first three-dimensional mesh by executing a marching cube algorithm. At step 908, a second three-dimensional mesh of a dose volume for the dosage is generated based on the second signal. For example, shared EP and RO workspace computing device 108 may execute one or more algorithms that operate on at least portions of the received dose matrix data to generate the second three-dimensional mesh of the dose volume. In some examples, shared EP and RO workspace computing device 108 calculates the second three-dimensional mesh by first generating a voxelized volume of the heart substructures and then executing a marching cube algorithm.

At step 910, the second three-dimensional mesh of the dose volume is superimposed over the first three dimensional mesh of the organ to generate a third three-dimensional mesh. At step 912, the third three-dimensional mesh is displayed. For example, shared EP and RO workspace computing device 108 may display the three-dimensional mesh, which includes the second three-dimensional mesh of the dose volume is superimposed over the first three dimensional mesh of the organ, in a 3D viewer to a electrophysiologist. In some examples, shared EP and RO workspace computing device 108 generates a cardiac radioablation treatment plan based on the three-dimensional mesh. In some examples, shared EP and RO workspace computing device 108 transmits the cardiac radioablation treatment plan to a radiotherapy delivery system to deliver the dosage to a patient. The method then ends.

Figure 10:
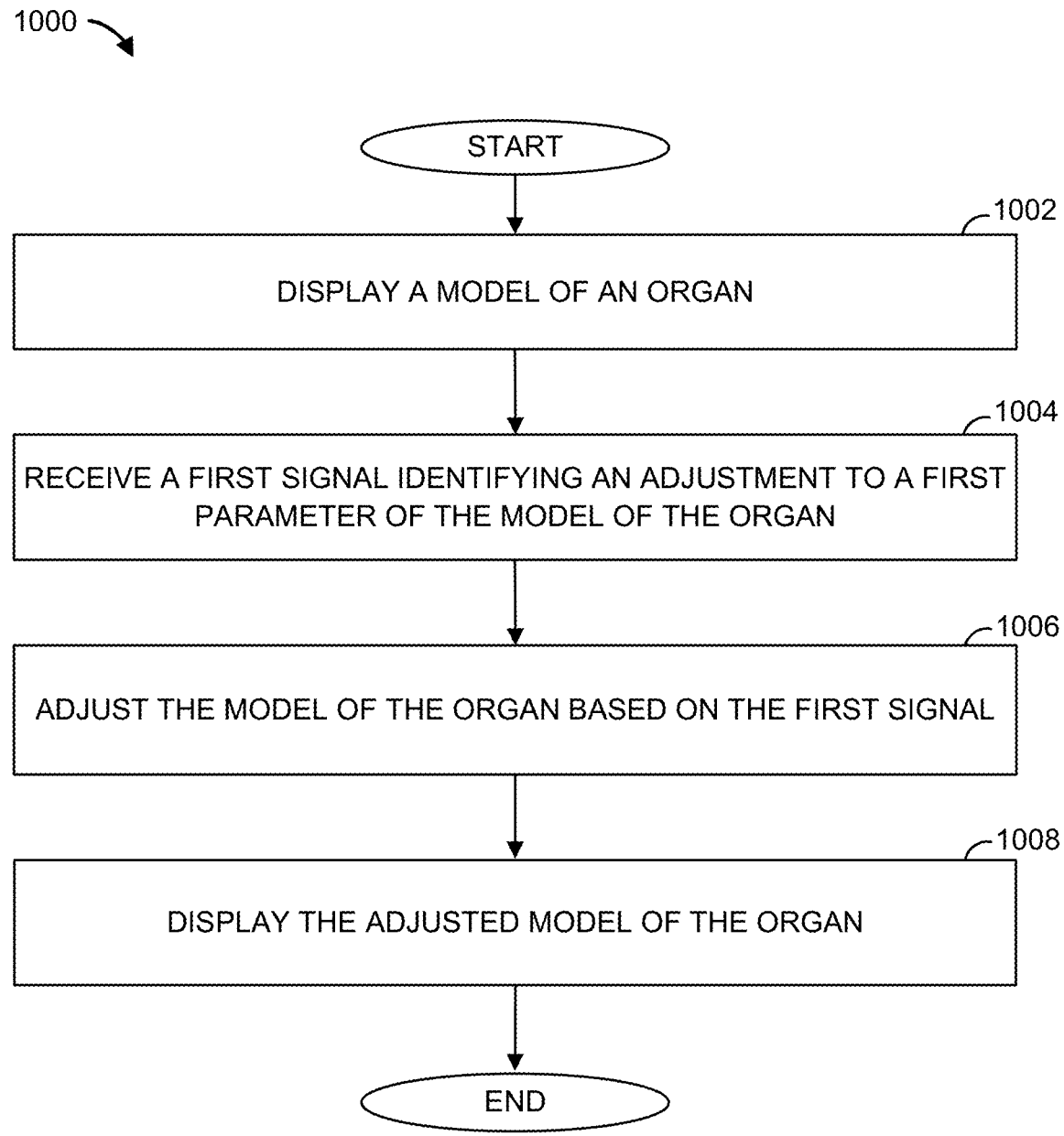
FIG. 10 is a flowchart of an example method to display an adjusted model of an organ, in accordance with some embodiments.

FIG. 10 is a flowchart of an example method 1000 that can be carried out by, for example, radioablation diagnosis and treatment planning computing device 200. Beginning at step 1002, the computing device 200 displays a model of an organ. At step 1004, the computing device 200 receives a first signal identifying an adjustment to a first parameter of the model of the organ. Proceeding to step 1006, the computing device 200 adjusts the model of the organ based on the first signal. For example, the computing device 200 may adjust the first parameter in accordance with the first signal, and may regenerate the model of the organ based on the adjusted first parameter. At step 1008, the computing device displays the adjusted model of the organ. For example, the computing device 200 may display a three-dimensional model of the organ. The method then ends.

In some examples, a computer-implemented method includes receiving substructure data identifying substructure contours for an organ, and dose matrix data. The dota matrix data may identify a dosage for an organ, for example. The method also includes generating a first mesh of organ substructures for the organ based on the substructure data. The method also includes generating a second mesh of an isodose volume based on the dose matrix data. Further, the method includes displaying the first mesh of the organ substructures and the second mesh of the isodose volume within a same scene.

In some examples, the method includes generating a voxelized volume of the substructure contours, and executing an image based meshing algorithm that operates on the voxelized volume of the substructure contours.

In some examples, the method includes obtaining a dose threshold value, and filtering the dose matrix data based on the dose threshold value. In some examples, the method includes executing a marching cube algorithm that operates on the filtered dose matrix data.

In some examples, the method includes associating a plurality of dose value ranges with a unique identifier, and determining the unique identifier for each of a plurality of surface points of the second mesh based on the plurality of dose value ranges. In some examples, the unique identifier is a color.

In some examples, the method includes determining each of a plurality of dosage values along a tangential line to each of the plurality of surface points. The method also includes determining a representative dosage value for each of the plurality of surface points based on the corresponding plurality of dosage values. The method further includes determining the unique identifier for each of the plurality of surface points based on the corresponding representative dosage value.

In some examples, the method includes mapping the unique identifier for each of the plurality of surface points to a segmentation model. The method also includes generating an image of the segmentation model based on the mapped unique identifiers. The method further includes displaying the image of the segmentation model.

In some examples, the method includes applying a color wash to the segmentation model based on the mapped unique identifiers.

In some examples, a non-transitory computer readable medium storing instructions that, when executed by at least one processor, cause the at least one processor to perform operations including receiving substructure data identifying substructure contours for an organ, and dose matrix data. The operations also include generating a first mesh of organ substructures for the organ based on the substructure data. Further, the operations include generating a second mesh of an isodose volume based on the dose matrix data. The operations also include displaying the first mesh of the organ substructures and the second mesh of the isodose volume within a same scene.

In some examples, the operations include generating a voxelized volume of the substructure contours, and executing an image based meshing algorithm that operates on the voxelized volume of the substructure contours.

In some examples, the operations include obtaining a dose threshold value, and filtering the dose matrix data based on the dose threshold value. In some examples, generating the second mesh of the isodose volume includes executing a marching cube algorithm that operates on the filtered dose matrix data.

In some examples, the operations include associating a plurality of dose value ranges with a unique identifier, and determining the unique identifier for each of a plurality of surface points of the second mesh based on the plurality of dose value ranges. In some examples, the unique identifier is a color.

In some examples, the operations include determining each of a plurality of dosage values along a tangential line to each of the plurality of surface points. The operations also include determining a representative dosage value for each of the plurality of surface points based on the corresponding plurality of dosage values. The operations further include determining the unique identifier for each of the plurality of surface points based on the corresponding representative dosage value.

In some examples, the operations include mapping the unique identifier for each of the plurality of surface points to a segmentation model. The operations also include generating an image of the segmentation model based on the mapped unique identifiers. The operations further include displaying the image of the segmentation model.

In some examples, the operations include applying a color wash to the segmentation model based on the mapped unique identifiers.

In some examples, a system includes a computing device that is configured to receive substructure data identifying substructure contours for an organ, and dose matrix data. The computing device is also configured to generate a first mesh of organ substructures for the organ based on the substructure data. Further, the computing device is configured to generate a second mesh of an isodose volume based on the dose matrix data. The computing is also configured to display the first mesh of the organ substructures and the second mesh of the isodose volume within a same scene of a 3D viewer or workspace.

In some examples, the computing device is configured to generate a voxelized volume of the substructure contours, and execute an image based meshing algorithm that operates on the voxelized volume of the substructure contours.

In some examples the computing device is configured to obtain a dose threshold value, and filter the dose matrix data based on the dose threshold value. In some examples, the computing device is configured to execute a marching cube algorithm that operates on the filtered dose matrix data.

In some examples, the computing device is configured to associate a plurality of dose value ranges with a unique identifier, and determine the unique identifier for each of a plurality of surface points of the second mesh based on the plurality of dose value ranges. In some examples, the unique identifier is a color.

In some examples, the computing device is configured to determine each of a plurality of dosage values along a tangential line to each of the plurality of surface points. The computing device is also configured to determine a representative dosage value for each of the plurality of surface points based on the corresponding plurality of dosage values. The computing device is further configured determine the unique identifier for each of the plurality of surface points based on the corresponding representative dosage value.

In some examples, the computing device is configured to map the unique identifier for each of the plurality of surface points to a segmentation model. The computing device is configured to generate an image of the segmentation model based on the mapped unique identifiers. The computing device is also configured to display the image of the segmentation model.

In some examples, the computing device is configured to apply a color wash to the segmentation model based on the mapped unique identifiers.

In some examples, a method includes a means for receiving substructure data identifying substructure contours for an organ, and dose matrix data. The method also includes a means for generating a first mesh of organ substructures for the organ based on the substructure data. The method also includes a means for generating a second mesh of an isodose volume based on the dose matrix data. Further, the method includes a means for displaying the first mesh of the organ substructures and the second mesh of the isodose volume within a same scene of a 3D viewer or workspace.

In some examples, the method includes a means for generating a voxelized volume of the substructure contours, and a means for executing a marching cube algorithm that operates on the voxelized volume of the substructure contours.

In some examples, the method includes a means for obtaining a dose threshold value, and filtering the dose matrix data based on the dose threshold value. In some examples, the method includes a means for executing a marching cube algorithm that operates on the filtered dose matrix data.

In some examples, the method includes a means for associating a plurality of dose value ranges with a unique identifier, and determining the unique identifier for each of a plurality of surface points of the second mesh based on the plurality of dose value ranges. In some examples, the unique identifier is a color.

In some examples, the method includes a means for determining each of a plurality of dosage values along a tangential line to each of the plurality of surface points. The method also includes a means for determining a representative dosage value for each of the plurality of surface points based on the corresponding plurality of dosage values. The method further includes a means for determining the unique identifier for each of the plurality of surface points based on the corresponding representative dosage value.

In some examples, the method includes a means for mapping the unique identifier for each of the plurality of surface points to a segmentation model. The method also includes generating an image of the segmentation model based on the mapped unique identifiers. The method further includes a means for displaying the image of the segmentation model.

In some examples, the method includes a means for applying a color wash to the segmentation model based on the mapped unique identifiers.

Although the methods described above are with reference to the illustrated flowcharts, it will be appreciated that many other ways of performing the acts associated with the methods can be used. For example, the order of some operations may be changed, and some of the operations described may be optional.

In addition, the methods and system described herein can be at least partially embodied in the form of computer-implemented processes and apparatus for practicing those processes. The disclosed methods may also be at least partially embodied in the form of tangible, non-transitory machine-readable storage media encoded with computer program code. For example, the steps of the methods can be embodied in hardware, in executable instructions executed by a processor (e.g., software), or a combination of the two. The media may include, for example, RAMs, ROMs, CD-ROMs, DVD-ROMs, BD-ROMs, hard disk drives, flash memories, or any other non-transitory machine-readable storage medium. When the computer program code is loaded into and executed by a computer, the computer becomes an apparatus for practicing the method. The methods may also be at least partially embodied in the form of a computer into which computer program code is loaded or executed, such that, the computer becomes a special purpose computer for practicing the methods. When implemented on a general-purpose processor, the computer program code segments configure the processor to create specific logic circuits. The methods may alternatively be at least partially embodied in application specific integrated circuits for performing the methods.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A computer-implemented method comprising:
   receiving substructure data identifying substructure contours of an organ, and dose matrix data;
   generating a first mesh of organ substructures for the organ based on the substructure data;
   obtaining a dose threshold value;
   generating a second mesh of an isodose volume based on filtering the dose matrix data based on the dose threshold value; and
   displaying the first mesh of the organ substructures and the second mesh of the isodose volume within a same scene.

2. The computer-implemented method of claim 1 wherein generating the first mesh of organ substructures comprises:
   generating a voxelized volume of the substructure contours; and
   executing an image based meshing algorithm that operates on the voxelized volume of the substructure contours.

3. The computer-implemented method of claim 1 wherein generating the second mesh of the isodose volume comprises executing an image based meshing algorithm that operates on the filtered dose matrix data.

4. The computer-implemented method of claim 1 wherein the organ is a heart.

5. The computer-implemented method of claim 1 wherein generating the second mesh of the isodose volume comprises associating a plurality of dose value ranges with a unique identifier; and determining the unique identifier for each of a plurality of surface points of the second mesh based on the plurality of dose value ranges.

6. The computer-implemented method of claim 5 wherein determining the unique identifier for each of the plurality of surface points of the second mesh comprises:
   determining each of a plurality of dosage values along a tangential line to each of the plurality of surface points;
   determining a representative dosage value for each of the plurality of surface points based on the corresponding plurality of dosage values; and
   determining the unique identifier for each of the plurality of surface points based on the corresponding representative dosage value.

7. The computer-implemented method of claim 6 comprising:
   mapping the unique identifier for each of the plurality of surface points to a segmentation model;
   generating an image of the segmentation model based on the mapped unique identifiers; and
   displaying the image of the segmentation model.

8. The computer-implemented method of claim 7 wherein generating the image of the segmentation model comprises applying a color wash to the segmentation model based on the mapped unique identifiers.

9. The computer-implemented method of claim 5 wherein the unique identifier is a color.

10. A non-transitory computer readable medium storing instructions that, when executed by at least one processor, cause the at least one processor to perform operations comprising:
    receiving substructure data identifying substructure contours for an organ, and dose matrix data;
    generating a first mesh of organ substructures for the organ based on the substructure data;
    obtaining a dose threshold value;
    generating a second mesh of an isodose volume based on filtering the dose matrix data based on the dose threshold value; and
    displaying the first mesh of the organ substructures and the second mesh of the isodose volume within a same scene.

11. The non-transitory computer readable medium of claim 10 wherein generating the first mesh of organ substructures comprises:
    generating a voxelized volume of the substructure contours; and
    executing an image based meshing algorithm that operates on the voxelized volume of the substructure contours.

12. The non-transitory computer readable medium of claim 10 wherein generating the second mesh of the isodose volume comprises associating a plurality of dose value ranges with a unique identifier; and determining the unique identifier for each of a plurality of surface points of the second mesh based on the plurality of dose value ranges.

13. The non-transitory computer readable medium of claim 12 wherein determining the unique identifier for each of the plurality of surface points of the second mesh comprises:
    determining each of a plurality of dosage values along a tangential line to each of the plurality of surface points;
    determining a representative dosage value for each of the plurality of surface points based on the corresponding plurality of dosage values; and determining the unique identifier for each of the plurality of surface points based on the corresponding representative dosage value.

14. The non-transitory computer readable medium of claim 13 wherein the operations further comprise:
mapping the unique identifier for each of the plurality of surface points to a segmentation model;
generating an image of the segmentation model based on the mapped unique identifiers; and
displaying the image of the segmentation model.

15. A system comprising:
a computing device configured to:
receive-substructure data identifying substructure contours for an organ, and dose matrix data;
generate a first mesh of organ substructures for the organ based on the substructure data;
obtain a dose threshold value;
generate a second mesh of an isodose volume based on filtering the dose matrix data based on the dose threshold value; and
display the first mesh of the organ substructures and the second mesh of the isodose volume within a same scene.

16. The system of claim 15, wherein to generate the first mesh of organ substructures, the computing device is configured to:
generate a voxelized volume of the substructure contours; and
execute an image based meshing algorithm that operates on the voxelized volume of the substructure contours.

17. The system of claim 15, wherein to generate the second mesh of the isodose volume, the computing device is configured to associate a plurality of dose value ranges with a unique identifier; and determine the unique identifier for each of a plurality of surface points of the second mesh based on the plurality of dose value ranges.

18. The system of claim 17, wherein to determine the unique identifier for each of the plurality of surface points of the second mesh, the computing device is configured to:
determine each of a plurality of dosage values along a tangential line to each of the plurality of surface points;
determine a representative dosage value for each of the plurality of surface points based on the corresponding plurality of dosage values; and
determine the unique identifier for each of the plurality of surface points based on the corresponding representative dosage value.

19. The system of claim 18, wherein the computing device is configured to:
map the unique identifier for each of the plurality of surface points to a segmentation model;
generate an image of the segmentation model based on the mapped unique identifiers; and
display the image of the segmentation model.

20. The system of claim 15, wherein to generate the second mesh of the isodose volume, the computing device is configured to execute an image based meshing algorithm that operates on the filtered dose matrix data.

* * * * *